(12) United States Patent
Hotta et al.

(10) Patent No.: US 8,766,248 B2
(45) Date of Patent: Jul. 1, 2014

(54) NITROGEN-CONTAINING AROMATIC COMPOUND, ORGANIC SEMICONDUCTOR MATERIAL, AND ORGANIC ELECTRONIC DEVICE

(75) Inventors: Masanori Hotta, Kitakyushu (JP); Yuichi Sawada, Kitakyushu (JP); Atsushi Kawada, Kitakyushu (JP); Masana Jikumaru, Kitakyushu (JP); Megumi Matsumoto, Kitakyushu (JP)

(73) Assignee: Nippon Steel & Sumikin Chemical Co., Ltd., Tokyo (JP)

( * ) Notice: Subject to any disclaimer, the term of this patent is extended or adjusted under 35 U.S.C. 154(b) by 0 days.

(21) Appl. No.: 13/818,685

(22) PCT Filed: Jul. 7, 2011

(86) PCT No.: PCT/JP2011/065554
§ 371 (c)(1),
(2), (4) Date: Feb. 25, 2013

(87) PCT Pub. No.: WO2012/035853
PCT Pub. Date: Mar. 22, 2012

(65) Prior Publication Data
US 2013/0150576 A1 Jun. 13, 2013

(30) Foreign Application Priority Data

Sep. 13, 2010 (JP) .................................. 2010-204102
Dec. 6, 2010 (JP) .................................. 2010-271873

(51) Int. Cl.
*C07D 487/02* (2006.01)
*C07D 491/048* (2006.01)
*C07D 495/04* (2006.01)

(52) U.S. Cl.
USPC ........................................... 257/40; 548/421

(58) Field of Classification Search
USPC ........................................... 548/421; 257/40
See application file for complete search history.

(56) References Cited

U.S. PATENT DOCUMENTS

2012/0001158 A1 1/2012 Asari et al.
2012/0273764 A1 11/2012 Yu et al.

FOREIGN PATENT DOCUMENTS

JP 2009-54809 A 3/2009
JP 2009-302328 A 12/2009

OTHER PUBLICATIONS

International Search Report for the Application No. PCT/JP2011/065554 mailed Aug. 2, 2011.
International Preliminary Report on Patentability for Application No. PCT/JP2011/065554 mailed Mar. 21, 2013.
Kienle, Marcel et al., "Preparation of Heterocyclic Amines by an Oxidative Amination of Zinc Organometallics Mediated by $Cu^1$: A New Oxidative Cycloamination for the Preparation of Annulated Indole Derivatives", Chemistry—An Asian Journal, 2011, vol. 6, pp. 517-523.
Klauk, Hagen et al., "High-mobility polymer gate dielectric pentacene thin film transistors", Journal of Applied Physics, Nov. 1, 2002, vol. 92, No. 9, pp. 5259-5263.
Holmes, R.J. et al., "Blue organic electrophosphorescence using exothermic host-guest energy transfer", Applied Physics Letters, Apr. 14, 2003, vol. 82, No. 15, pp. 2422-2424.

*Primary Examiner* — Shawquia Young
(74) *Attorney, Agent, or Firm* — Cheng Law Group, PLLC

(57) ABSTRACT

Provided are a nitrogen-containing aromatic heterocyclic compound useful as an organic semiconductor material and an organic electronic device using this compound. The nitrogen-containing aromatic heterocyclic compound has a fused indole skeleton represented by the following formula (1), the organic semiconductor material contains the compound, and the organic electronic device uses the organic semiconductor material. In general formula (1), X is N-A', O, S, or Se; A is an alkyl group, a cycloalkyl group, an alkenyl group, an alkynyl group, an aromatic hydrocarbon group, or an aromatic heterocyclic group exclusive of a fused heterocycle consisting of 4 rings or more; and R is a hydrogen atom, an alkyl group, a cycloalkyl group, an alkenyl group, an alkynyl group, an aromatic hydrocarbon group, or an aromatic heterocyclic group exclusive of a fused heterocycle consisting of 4 rings or more.

4 Claims, 3 Drawing Sheets

NITROGEN-CONTAINING AROMATIC COMPOUND, ORGANIC SEMICONDUCTOR MATERIAL, AND ORGANIC ELECTRONIC DEVICE

TECHNICAL FIELD

This invention relates to a novel nitrogen-containing aromatic compound and an organic electronic device using the said compound and, further, to a light-emitting device, a thin film transistor, and a photovoltaic device utilizing the said compound as an organic semiconductor material.

BACKGROUND TECHNOLOGY

In recent years, organic electronic devices in which organic compounds are used as semiconductor materials have enjoyed remarkable prosperity. Typical examples of their applications include organic electroluminescent devices (hereinafter referred to as organic EL device) that are expected to become next generation flat panel displays, organic thin film transistors (organic TFT) that are attracting attention on account of their ability to furnish thin film transistors to be used for driving pixels in displays by a low-cost process such as printing and to cope with flexible substrates, and photovoltaic devices (organic thin film solar cell) that provide lightweight and flexible power sources.

In the manufacture of a semiconductor device using silicon which is an inorganic semiconductor material, the forming of a thin film of silicon necessarily employs a high temperature process as well as a high vacuum process. The need of a high temperature process makes it impossible to form a thin film of silicon on a plastic substrate. Hence, it has been difficult to make a product in which a silicon-based semiconductor device is incorporated as a part flexible and lightweight. On the other hand, the need of a high vacuum process has made it difficult to enlarge the area and lower the cost of a product in which a semiconductor device is incorporated as a part.

An organic compound is easier to process than inorganic silicon and its use as a semiconductor material is expected to realize an inexpensive device. Further, a semiconductor device using an organic compound can be manufactured at low temperature and its application to a variety of substrates including plastic substrates becomes feasible. Still further, an organic semiconductor material is structurally soft and a combination of a plastic substrate and an organic semiconductor material is expected to be applied to the manufacture of organic semiconductor products in which the characteristics of the two in combination are fully utilized, for example, to the realization of flexible devices such as organic EL panels and electronic paper, liquid crystal displays, information tags, and large-area sensors such as artificial electronic skin sheets and sheet type scanners.

The organic semiconductor materials intended for use in the aforementioned organic electronic devices are in need of improvement of properties; for example, enhancement of the luminous efficiency, extension of the life, and reduction of the driving voltage in the case of organic EL devices, improvement of the charge mobility to lower the threshold voltage and improve the switching speed in the case of organic TFT devices, and enhancement of the photovoltaic conversion efficiency in the case of organic thin film solar cells.

For example, in the case of materials for organic EL devices, a host material that plays the role of charge transport in the light-emitting layer becomes important in order to enhance the luminous efficiency. Of the host materials proposed thus far, typical examples are 4,4'-bis(9-carbazolyl) biphenyl (hereinafter referred to as CBP), a carbazole compound presented in patent document 1, and 1,3-dicarbazolylbenzene (hereinafter referred to as mCP) presented in non-patent document 1. Since CBP is characterized by having a good hole transfer property but a poor electron transfer property, the use of CBP as a host material for tris(2-phenylpyridine)iridium complex (hereinafter referred to as Ir(ppy)$_3$), a typical phosphorescent green light-emitting material, disturbs the balanced injection of charges and causes an excess of holes to flow out to the side of the electron-transporting layer. The results is a reduction in the luminous efficiency of Ir(ppy)$_3$. On the other hand, the use of mCP as a host material for bis[2-(4,6-difluorophenyl)pyridinato-N, C2'] (picolinate) iridium complex (hereinafter referred to as FIrpic), a typical phosphorescent blue light-emitting material, displays relatively good luminous characteristics, but the compound is not satisfactory for practical use particularly from the viewpoint of durability.

As described above, host materials that are well balanced in the injection and transport characteristics of electric charges (holes and electrons) are required in order for organic EL devices to display high luminous efficiency, Furthermore, compounds that are electrochemically stable, highly resistant to heat, and excellently stable in the amorphous state are desirable and further improvements of properties are demanded.

In recent years, organic semiconductor materials that are comparable to amorphous silicon in charge transport characteristics are reported as useful for organic TFT devices. For example, non-patent document 2 presents an organic TFT device in which pentacene, an acene type polycyclic aromatic molecule formed by rectilinear fusion of five benzene rings, is used as an organic semiconductor material and reports that the device displays a charge mobility comparable to that of amorphous silicon. However, in the case where pentacene is used as an organic semiconductor material for an organic TFT device, a thin organic semiconductor film is formed from pentacene by the vapor deposition process in superhigh vacuum and this is disadvantageous from the viewpoint of making the film larger in area, flexible, and lighter in weight and reducing the cost. Further, patent document 2 proposes a method for forming crystals of pentacene in a dilute o-dichlorobenzene solution without using the vacuum vapor deposition process. However, the method is difficult to perform and it has not yet furnished a stable device. Another problem with acene type polycyclic aromatic hydrocarbon molecules such as pentacene is poor oxidation stability.

Studies on organic thin film solar cells had initially been conducted by the use of single-layer films made from merocyanine dyes and the like. Meanwhile, a multilayer film consisting of a p-layer that transports holes and an n-layer that transports electrons was found to improve the conversion efficiency of optical input to electric output (photovoltaic conversion efficiency) and thereafter the multilayer film design has become the mainstream. In the early days of studies on multilayer films, copper phthalocyanine (CuPc) was used for the p-layer and a peryleneimide (for example, PTCBI) for the n-layer. On the other hand, the studies on organic thin film solar cells using polymers were primarily focused on the so-called bulk heterojunction wherein an electrically conductive polymer used as a material for the p-layer and a fullerene (C60) derivative used as a material for the n-layer are mixed together and thermally treated to induce microphase separation thereby increasing the heterointerface and enhancing the photovoltaic conversion efficiency. The materials mainly used in these studies were poly(3-hexylthiophene) (P3HT) for the p-layer and C60 derivative (DCBM) for the n-layer.

As described above, not much progress has been achieved in the materials for both layers of organic thin film solar cells and phthalocyanine derivatives, peryleneimide derivatives, and C60 derivatives are still used today. Therefore, there has been a strong demand for development of novel materials to replace the conventional materials in order to enhance the photovoltaic conversion efficiency. For example, patent document 3 discloses an organic thin film solar cell in which a compound having a fluoranthene skeleton is used, but this does not yield satisfactory photovoltaic conversion efficiency.

Patent document 4 discloses the indoloindole compound illustrated below. However, the document merely discloses indoloindole compounds having a skeleton formed by [3,2-b] fusion and organic transistors using these compounds.

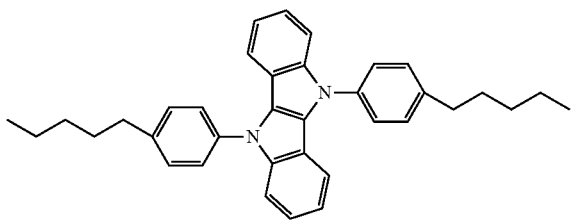 [SMILES: CCCCCc1ccc(-n2c3ccccc3c3c2c2ccccc2n3-c2ccc(CCCCC)cc2)cc1]

Patent documents 5 and 6 disclose organic EL devices using the compounds illustrated below. However, the documents merely disclose compounds having a benzochalcogeno[3,2-b]benzochalcogenophene skeleton and organic EL devices using these compounds.

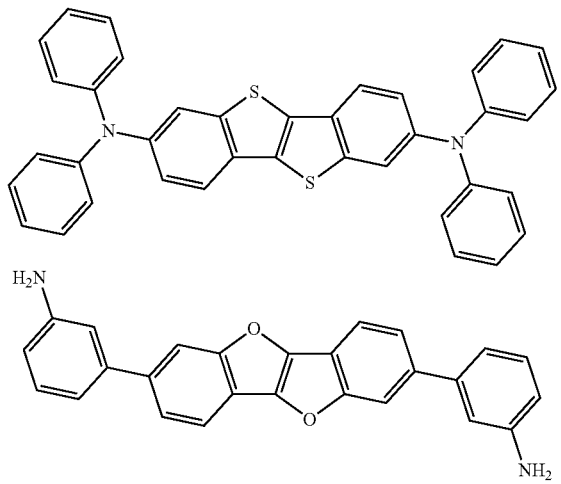

PRIOR ART TECHNICAL DOCUMENTS

Patent Documents

Patent document 1: JP 2001-313178 A
Patent document 2: WO 2003/016599 A
Patent document 3: JP 2009-290091 A
Patent document 4: JP 2009-054809 A
Patent document 5: JP 2009-246139 A
Patent document 6: JP 2009-246140 A Non-Patent Documents Non-patent document 1: Applied Physics Letters, 2003, 82, 2422-2424
Non-patent document 2: Journal of Applied Physics, 2002, 92, 5259-5263

DISCLOSURE OF THE INVENTION

An object of this invention is to provide a novel nitrogen-containing aromatic compound that can be used as an organic semiconductor material capable of solving the aforementioned problems concerned with the conventional technologies.

The inventors of this invention have conducted intensive studies, found that the use of a nitrogen-containing aromatic compound of a specified structure in an organic electronic device enhances charge mobility, and completed this invention.

This invention relates to a nitrogen-containing aromatic compound represented by general formula (1).

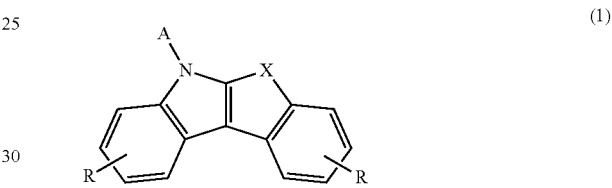

(1)

In formula (1), X is N-A', O, S, or Se; A is an alkyl group of 1 to 30 carbon atoms, a cycloalkyl group of 3 to 30 carbon atoms, an alkenyl group of 2 to 30 carbon atoms, an alkynyl group of 2 to 30 carbon atoms, an aromatic hydrocarbon group of 6 to 50 carbon atoms, or an aromatic heterocyclic group of 3 to 50 carbon atoms exclusive of a fused heterocycle consisting of 4 rings or more; each R is independently a hydrogen atom, an alkyl group of 1 to 30 carbon atoms, a cycloalkyl group of 3 to 30 carbon atoms, an alkenyl group of 2 to 30 carbon atoms, an alkynyl group of 2 to 30 carbon atoms, an aromatic hydrocarbon group of 6 to 30 carbon atoms, or an aromatic heterocyclic group of 3 to 30 carbon atoms exclusive of a fused heterocycle consisting of 4 rings or more; and A' is an alkyl group of 1 to 30 carbon atoms, a cycloalkyl group of 3 to 30 carbon atoms, an alkenyl group of 2 to 30 carbon atoms, an alkynyl group of 2 to 30 carbon atoms, an aromatic heterocyclic group-substituted aromatic hydrocarbon group of 6 to 50 carbon atoms, or an aromatic heterocyclic group of 3 to 50 carbon atoms exclusive of a fused heterocycle consisting of 4 rings or more.

Of the compounds represented by general formula (1), those in which X is N-A', are preferred.

Further, this invention relates to an organic semiconductor material containing the aforementioned nitrogen-containing aromatic compound and an organic electronic device using the said organic semiconductor material.

PREFERRED EMBODIMENTS OF THE INVENTION

Figure 1:
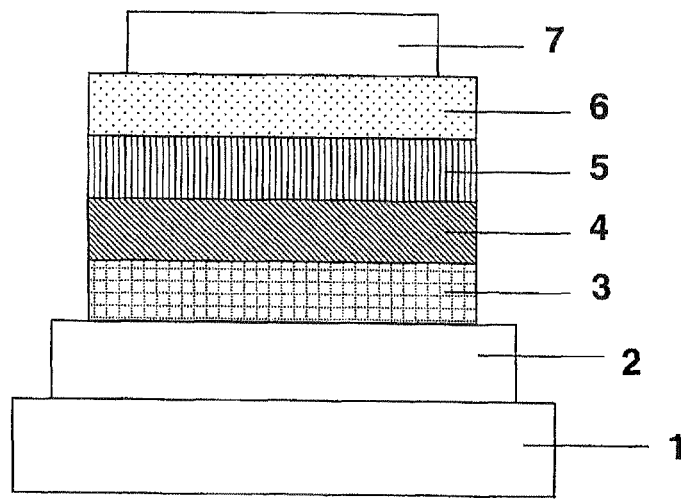
FIG. 1 is a schematic cross section illustrating an example of the structure of an organic EL device.

A nitrogen-containing aromatic compound according to this invention is represented by general formula (1). The nitrogen-containing aromatic compound of this invention is hereinafter referred to as compound of this invention or compound represented by general formula (1).

In general formula (1), X is N-A', O, S, or Se; preferably, X is N-A', O, or S and more preferably, X is N-A'.

In general formula (1), A is an alkyl group of 1 to 30 carbon atoms, a cycloalkyl group of 3 to 30 carbon atoms, an alkenyl group of 2 to 30 carbon atoms, an alkynyl group of 2 to 30 carbon atoms, an aromatic hydrocarbon group of 6 to 50 carbon atoms, or an aromatic heterocyclic group of 3 to 50 carbon atoms exclusive of a fused heterocycle consisting of 4 rings or more; preferably, A is an alkyl group of 1 to 20 carbon atoms, a cycloalkyl group of 3 to 20 carbon atoms, an alkenyl group of 2 to 20 carbon atoms, an alkynyl group of 2 to 20 carbon atoms, an aromatic hydrocarbon group of 6 to 30 carbon atoms, or an aromatic heterocyclic group of 3 to 30 carbon atoms exclusive of a fused heterocycle consisting of 4 rings or more.

The group A' is an alkyl group of 1 to 30 carbon atoms, a cycloalkyl group of 3 to 30 carbon atoms, an alkenyl group of 2 to 30 carbon atoms, an alkynyl group of 2 to 30 carbon atoms, an aromatic heterocyclic group-substituted aromatic hydrocarbon group of 6 to 50 carbon atoms, or an aromatic heterocyclic group of 3 to 50 carbon atoms exclusive of a fused heterocycle consisting of 4 rings or more; preferably, A' is an alkyl group of 1 to 20 carbon atoms, a cycloalkyl group of 3 to 20 carbon atoms, an alkenyl group of 2 to 20 carbon atoms, an alkynyl group of 2 to 20 carbon atoms, an aromatic heterocyclic group-substituted aromatic hydrocarbon group of 6 to 30 carbon atoms, or an aromatic heterocyclic group of 3 to 30 carbon atoms exclusive of a fused heterocycle consisting of 4 rings or more. A differs from A' in the case where each of them is an aromatic hydrocarbon group of 6 to 30 carbon atoms. In other cases, A is common with A'. Furthermore, A may be identical with A' in general formula (1).

In the case where A or A' is an alkyl group of 1 to 30 carbon atoms, the number of carbon atoms in the group is preferably 1 to 20, more preferably 1 to 10. Specific examples of the alkyl groups in the absence of substituents include a methyl group, an ethyl group, a propyl group, a butyl group, a pentyl group, a hexyl group, a heptyl group, an octyl group, a nonyl group, and a decyl group. Preferable examples include a methyl group, an ethyl group, a propyl group, a butyl group, a pentyl group, a hexyl group, a heptyl group, and an octyl group. The aforementioned alkyl groups may be linear or branched.

The aforementioned alkyl group may have substituents and, in the case where substituents are present, examples of substituents include a cycloalkyl group of 3 to 11 carbon atoms, an aromatic hydrocarbon group of 6 to 18 carbon atoms, and an aromatic heterocyclic group of 3 to 18 carbon atoms.

In the case where the aforementioned alkyl group has substituents, the total number of substituents is 1 to 10, preferably 1 to 6, more preferably 1 to 4. When there are two substituents or more, they may be identical with or different from one another.

In computing the number of carbon atoms in this specification, the number of carbon atoms in a substituent if any is included in the total number.

In the case where A or A' is a cycloalkyl group of 3 to 30 carbon atoms, the number of carbon atoms in the group is preferably 3 to 20, more preferably 5 to 10. Specific examples of the cycloalkyl groups in the absence of substituents include a cyclopropyl group, a cyclobutyl group, a cyclopentyl group, a cyclohexyl group, a cycloheptyl group, a cyclooctyl group, and a decahydronaphthyl group. Preferable examples include a cyclopentyl group and a cyclohexyl group.

Any of the aforementioned cycloalkyl groups may have substituents and, in the case where substituents are present, examples of substituents include an alkyl group of 1 to 10 carbon atoms, an aromatic hydrocarbon group of 6 to 18 carbon atoms, and an aromatic heterocyclic group of 3 to 18 carbon atoms.

In the case where any of the aforementioned cycloalkyl groups has substituents, the total number of substituents is 1 to 10, preferably 1 to 6, more preferably 1 to 4. When there are two substituents or more, they may be identical with or different from one another.

In the case where A or A' is an alkenyl group of 2 to 30 carbon atoms or an alkynyl group of 2 to 30 carbon atoms, the number of carbon atoms in the group is preferably 2 to 20, more preferably 2 to 10. Specific examples of the alkenyl group and the alkynyl group in the absence of substituents include an ethylenyl group, a propylenyl group, a butenyl group, a pentenyl group, a hexenyl group, a heptenyl grup, an octenyl group, an acetylenyl group, a propynyl group, a butynyl group, and a pentynyl group. Preferable examples include an ethylenyl group, a propylenyl group, a butenyl group, an acetylenyl group, and a propynyl group. The aforementioned alkenyl and alkynyl groups may be linear or branched.

The aforementioned alkenyl or alkynyl group may have substituents and, in the case where there are substituents, examples of substituents include a cycloalkyl group of 3 to 11 carbon atoms, an aromatic hydrocarbon group of 6 to 18 carbon atoms, and an aromatic heterocyclic group of 3 to 18 carbon atoms.

In the case where A is an aromatic hydrocarbon group of 6 to 50 carbon atoms, the number of carbon atoms in the group is preferably 6 to 30, more preferably 6 to 18. In the case where A' is an aromatic heterocyclic group-substituted aromatic hydrocarbon group of 6 to 50 carbon atoms, the number of carbon atoms in the group is preferably 6 to 30, more preferably 6 to 18. In the case where A or A' is an aromatic heterocyclic group of 3 to 50 carbon atoms, the number of carbon atoms in the group is preferably 3 to 30, more preferably 3 to 18. Here, the aromatic heterocyclic group does not contain a fused heterocycle consisting of 4 rings or more.

Specific examples of the aromatic hydrocarbon group and the aromatic heterocyclic group in the absence of substituents include monovalent groups formed by removing a hydrogen atom from benzene, pentalene, indene, naphthalene, azulene, heptalene, octalene, indacene, acenaphthylene, phenalene, phenanthrene, anthracene, trindene, fluoranthene, acephenanthrylene, aceanthrylene, triphenylene, pyrene, chrysene, tetraphene, tetracene, pleiadene, picene, perylene, pentaphene, pentacene, tetraphenylene, cholanthrylene, helicene, hexaphene, rubicene, coronene, trinaphthylene, heptaphene, pyranthrene, furan, benzofuran, isobenzofuran, xanthene, oxanthrene, dibenzofuran, perixanthenoxanthene, thiophene, thioxanthene, thianthrene, phenoxathiine, thionaphthene, isothianaphthene, thiophthene, thiophanthrene, dibenzothiophene, pyrrole, pyrazole, tellurazole, selenazole, thiazole, isothiazole, oxazole, furazan, pyridine, pyrazine, pyrimidine, pyridazine, triazine, indolizine, indole, isoindole, indazole, purine, quinolizine, isoquinoline, carbazole, imidazole, naphthyridine, phthalazine, quinazoline, benzodiazepine, quinoxaline, cinnoline, quinoline, pteridine, phenanthridine, acridine, perimidine, phenanthroline, phenazine, carboline, phenotellurazine, phenoselenazine, phenothiazine, phenoxazine, anthyridine, benzothiazole, benzimidazole, benzoxazole, benzisoxazole, and benzoisothiazole or from aromatic compounds in which a plurality of these aromatic rings are linked together. Preferable examples include monovalent groups formed by removing a hydrogen atom from benzene, naphthalene, anthracene, pyridine, pyrazine, pyrimidine, pyridazine, triazine, isoindole, indazole, purine, isoquinoline, imidazole, naphthyridine, phthalazine, quinazoline, benzodiazepine, quinoxaline, cinnoline, quinoline, pteridine, phenanthridine, acridine, perimidine, phenanthroline, phenazine, carboline, indole, carbazole, dibenzofuran, and dibenzothiophene or from aromatic compounds in which a plurality of these aromatic rings are linked together.

In the case where the groups in question are formed from aromatic compounds in which a plurality of these aromatic rings are linked together, the number of linked rings is preferably 2 to 10, more preferably 2 to 7, and the aromatic rings to be linked may be identical with or different from one another. In such a case, the position at which A is linked to the nitrogen atom is not limited and it may be a ring at the end or in the middle of the linked aromatic rings. Here, the aromatic ring is used as a general term to mean both an aromatic hydrocarbon ring and an aromatic heterocycle. In the case where a group consisting of linked aromatic rings contains at least one heterocycle, the group is included in aromatic heterocyclic groups.

The monovalent groups derived from compounds in which a plurality of aromatic rings are linked together are represented, for example, by the following formulas.

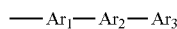

(11)

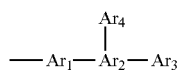

(12)

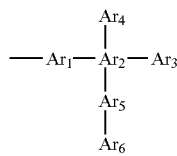

(13)

(In formulas (11) to (13), each of $Ar_1$ to $Ar_6$ is a substituted or unsubstituted aromatic ring.)

Specific examples of the aforementioned groups formed from compounds in which a plurality of aromatic rings are linked together include monovalent groups formed by removing a hydrogen atom from biphenyl, terphenyl, bipyridine, bipyrimidine, bitriazine, terpyridine, bistriazylbenzene, dicarbazolylbenzene, carbazolylbiphenyl, dicarbazolylbiphenyl, phenylterphenyl, carbazolylterphenyl, binaphthalene, phenylpyridine, phenylcarbazole, diphenylcarbazole, diphenylpyridine, diphenylpyrimidine, diphenylpyrimidine, phenyltriazine, diphenyltriazine, phenylnaphthalene, and diphenylnaphthalene.

An aromatic heterocyclic group exclusive of a fused heterocycle consisting of 4 rings or more means an aromatic heterocyclic group consisting of a single ring or a fused aromatic heterocyclic group consisting of 2 or 3 rings and the group may have substituents. In the case where this aromatic heterocyclic group consists of a plurality of aromatic rings linked together in the manner represented, for example, by formula (11), each of these aromatic rings can never be a fused heterocycle consisting of 4 rings or more.

The aforementioned aromatic hydrocarbon group or aromatic heterocyclic group may have substituents. When substituents are present, examples of such substituents include an alkyl group of 1 to 20 carbon atoms, a cycloalkyl group of 3 to 20 carbon atoms, an alkoxyl group of 1 to 2 carbon atoms, an acetyl group, an amino group of 6 to 18 carbon atoms, a phosphanyl group of 6 to 18 carbon atoms, and a silyl group of 3 to 18 carbon atoms. Preferable examples include an alkyl group of 1 to 4 carbon atoms, a cycloalkyl group of 3 to 6 carbon atoms, and an amino group of 6 to 15 carbon atoms. In this case, an aromatic group linked as a branch is not treated as a substituent.

In the case where A or A' is an aromatic hydrocarbon group or an aromatic heterocyclic group and has substituents, the total number of such substituents is 1 to 10, preferably 1 to 6, more preferably 1 to 4. In the case where two or more substituents are present, they may be identical with or different from one another.

In general formula (1), each R is independently a hydrogen atom, an alkyl group of 1 to 30 carbon atoms, a cycloalkyl group of 3 to 30 carbon atoms, an alkenyl group of 2 to 30 carbon atoms, an alkynyl group of 2 to 30 carbon atoms, an aromatic hydrocarbon group of 6 to 30 carbon atoms, or an aromatic heterocyclic group of 3 to 30 carbon atoms exclusive of a fused heterocycle consisting of 4 rings or more; preferably each R is independently a hydrogen atom, an alkyl group of 1 to 20 carbon atoms, a cycloalkyl group of 3 to 20 carbon atoms, an alkenyl group of 2 to 20 carbon atoms, an alkynyl group of 2 to 20 carbon atoms, an aromatic hydrocarbon group of 6 to 20 carbon atoms, or an aromatic heterocyclic group of 3 to 20 carbon atoms exclusive of a fused heterocycle consisting of 4 rings or more.

Specific examples of the alkyl group, cycloalkyl group, alkenyl group, or alkynyl group are the same as those of the aforementioned alkyl group, cycloalkyl group, alkenyl group, or alkynyl group constituting A. This holds for specific examples of substituents in the case where the alkyl group, cycloalkyl group, alkenyl group, or alkynyl group has substituents.

Specific examples of the aromatic hydrocarbon group or the aromatic heterocyclic group exclusive of a fused heterocycle consisting of 4 rings or more are the same as those of the aforementioned aromatic hydrocarbon group or aromatic heterocyclic group exclusive of a fused heterocycle consisting of 4 rings or more constituting A except for the difference in the total number of carbon atoms. Further, in the case where the aromatic hydrocarbon group or the aromatic heterocyclic group exclusive of a fused heterocycle consisting of 4 rings or more has substituents, specific examples of such substituents are the same as those of the substituents existing on the aforementioned groups constituting A.

A nitrogen-containing aromatic compound according to this invention can be synthesized by a known method by using an indole derivative as a starting material and selecting raw materials according to the structure of the target compound.

For example, a compound having a skeleton represented by general formula (1) wherein X is N-A' can be synthesized according to the reaction scheme shown below with reference to synthetic examples described in J. C. S. Chem. Comm., 1975, 911-912 and Journal of Chemical Research, 1988, 272-273.

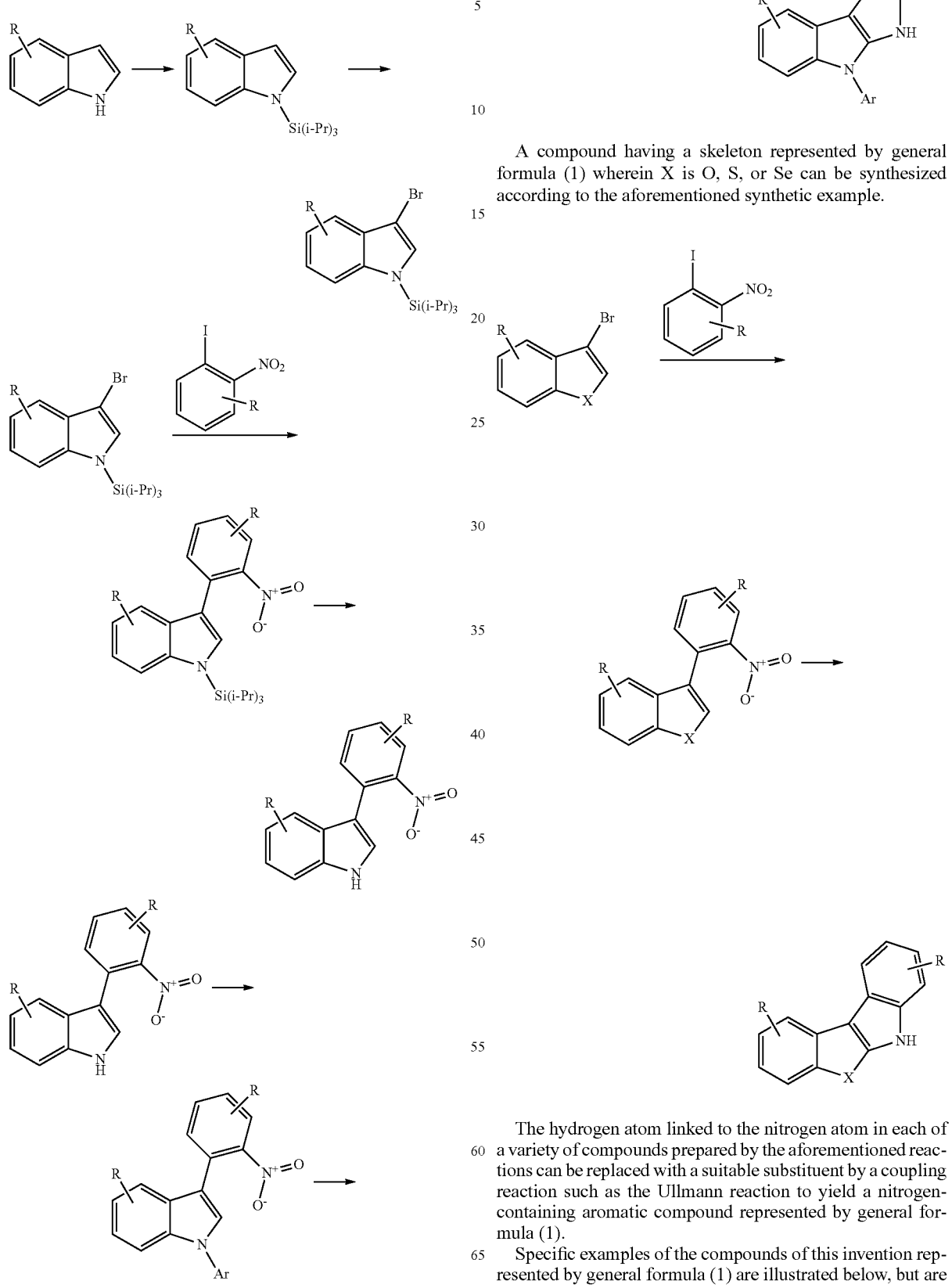

A compound having a skeleton represented by general formula (1) wherein X is O, S, or Se can be synthesized according to the aforementioned synthetic example.

The hydrogen atom linked to the nitrogen atom in each of a variety of compounds prepared by the aforementioned reactions can be replaced with a suitable substituent by a coupling reaction such as the Ullmann reaction to yield a nitrogen-containing aromatic compound represented by general formula (1).

Specific examples of the compounds of this invention represented by general formula (1) are illustrated below, but are not limited thereto.

11                                          12
                                            1-8                                       1-9
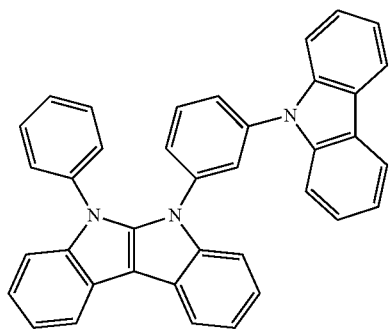                        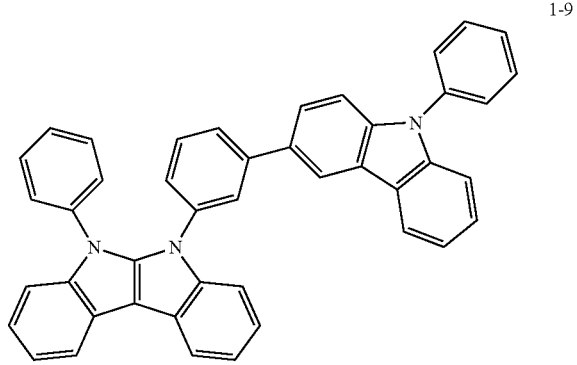
                                            1-10                                      1-11
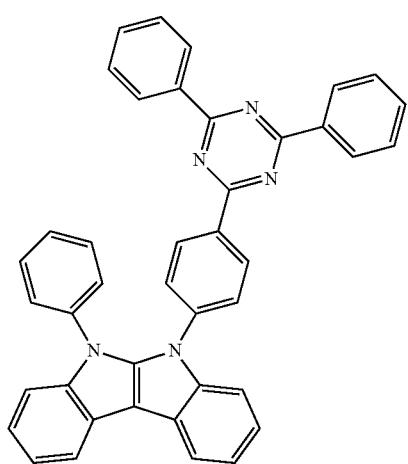                        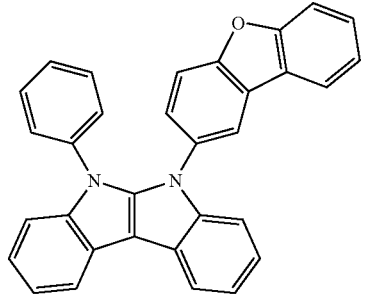
                                            1-12                                      1-13
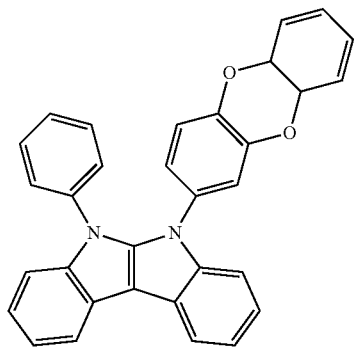                        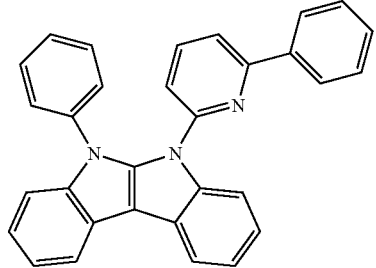

-continued
1-14
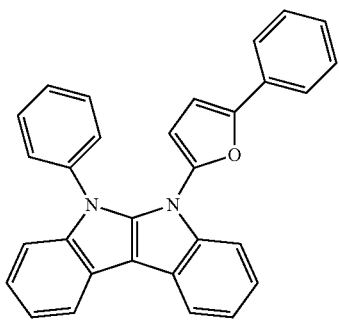
1-15
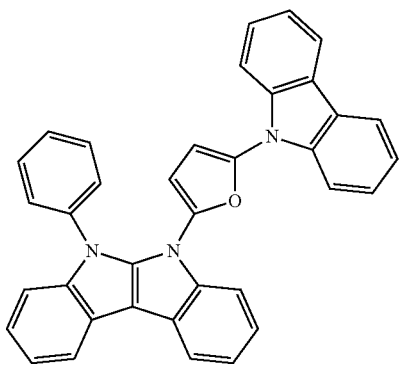
1-16
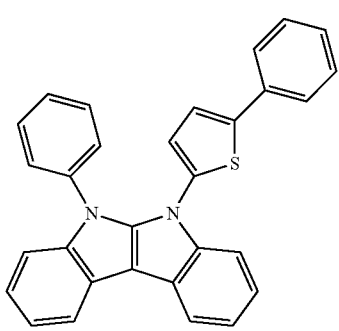
1-17
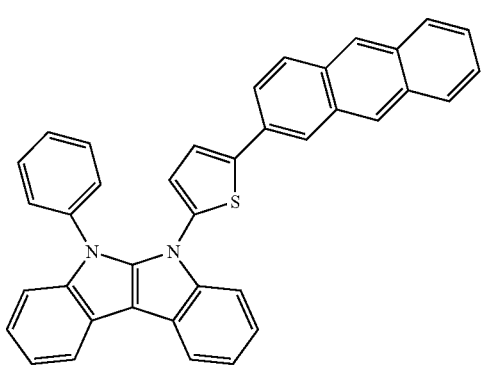
1-18
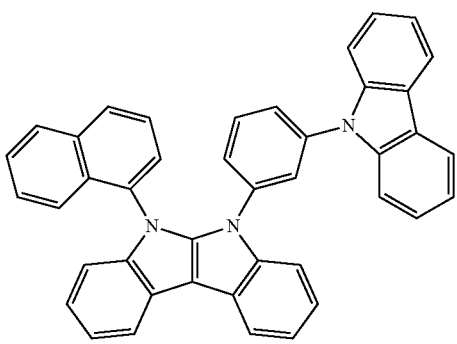
1-19
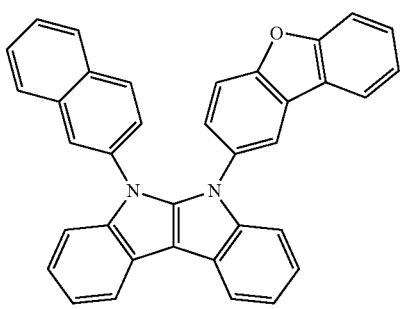
1-20
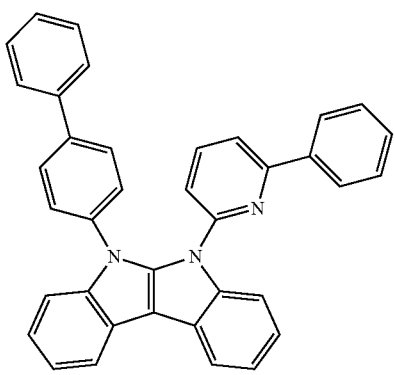
1-21
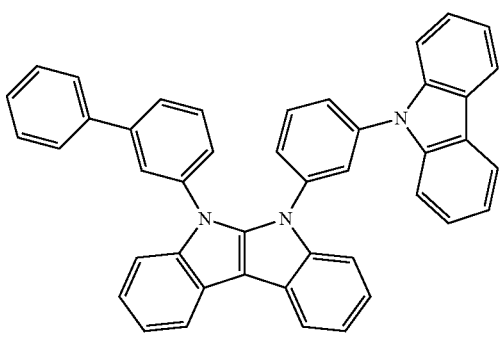

-continued
1-22
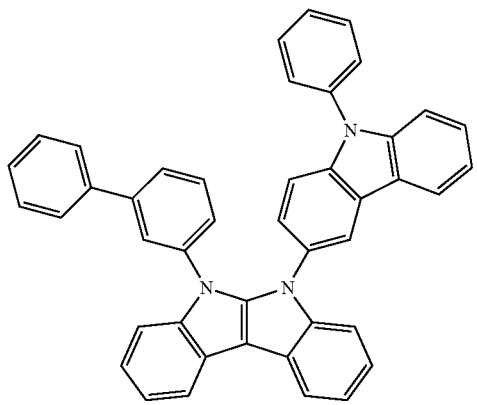
1-23
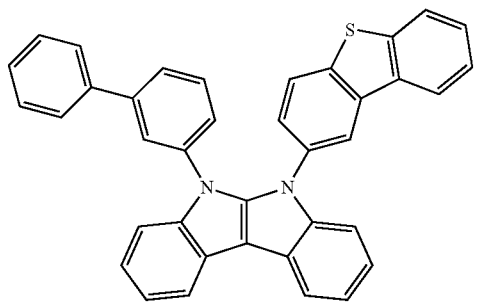
1-24
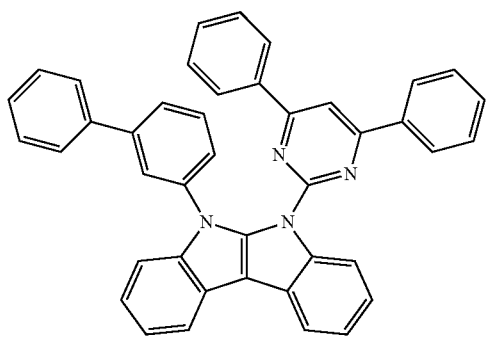
1-25
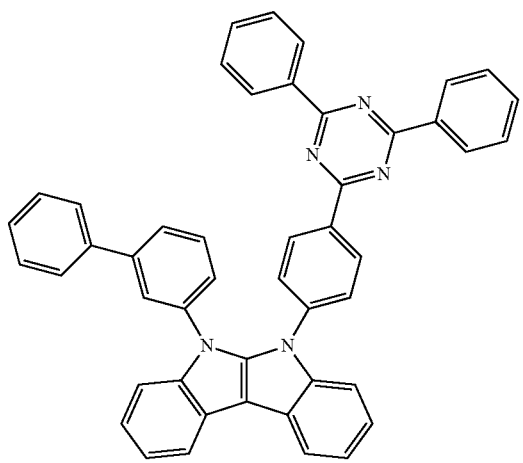
1-26
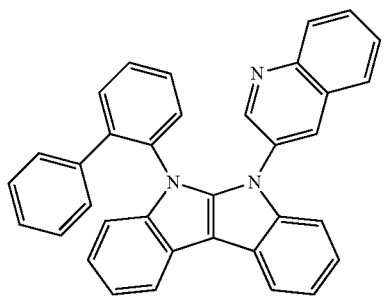
1-27
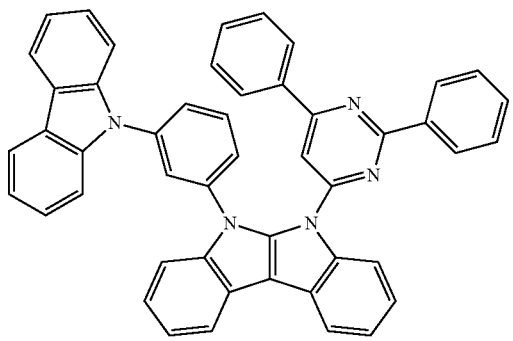

-continued
1-28
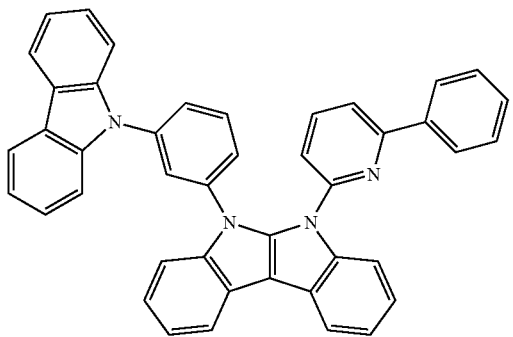
1-29
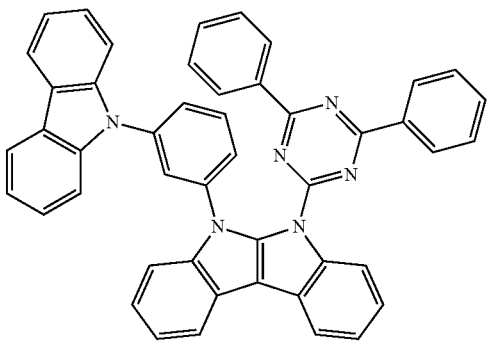
1-30
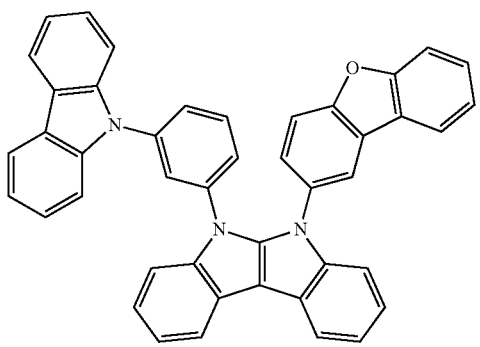
1-31
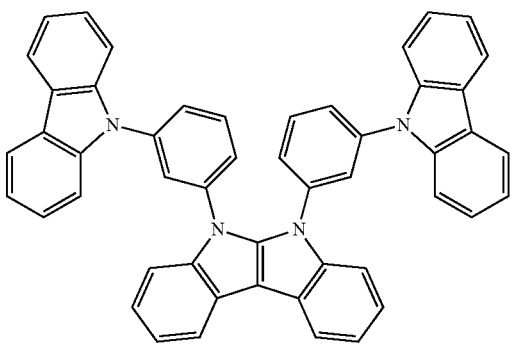
1-32
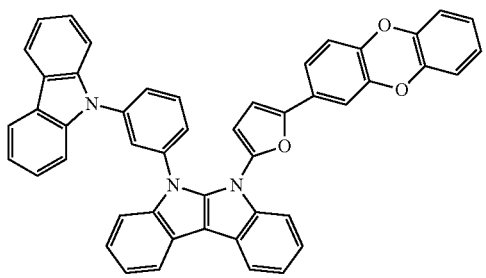
1-33
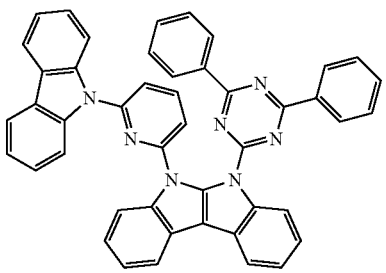
1-34
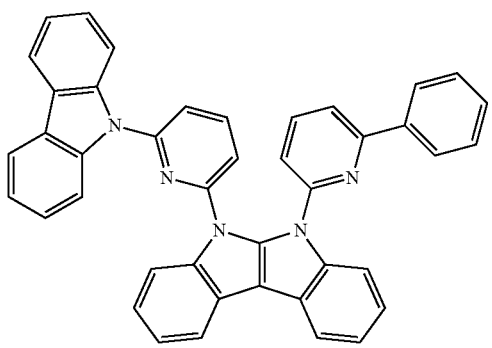

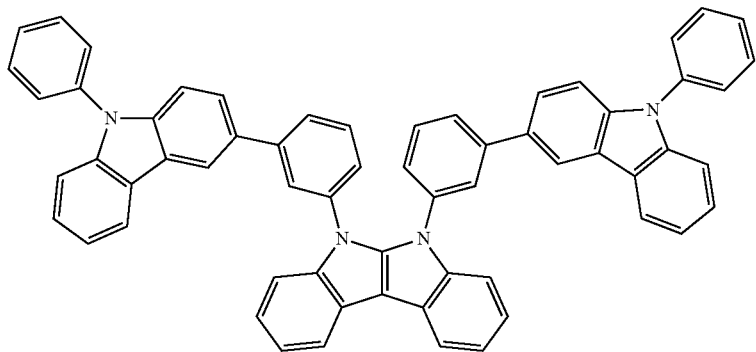
1-35
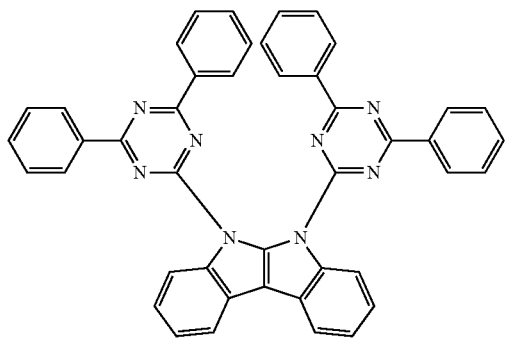
1-36
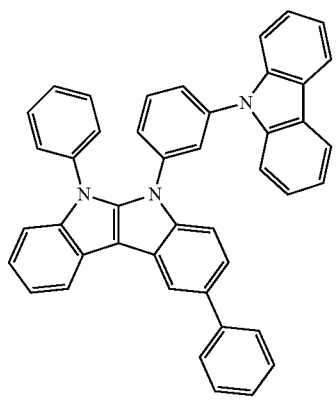
1-37
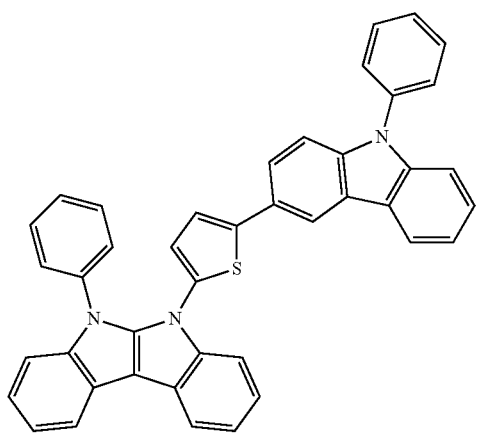
1-38
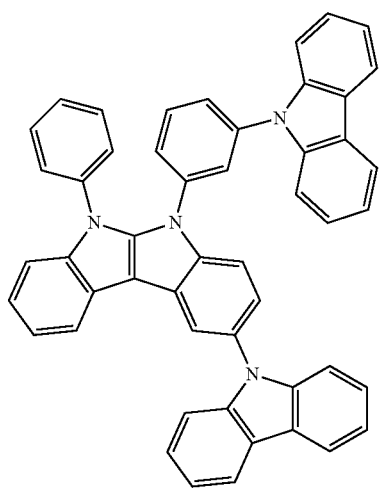
1-40

-continued
1-41
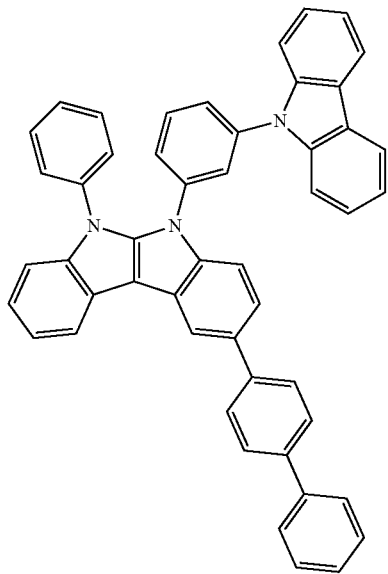
1-42
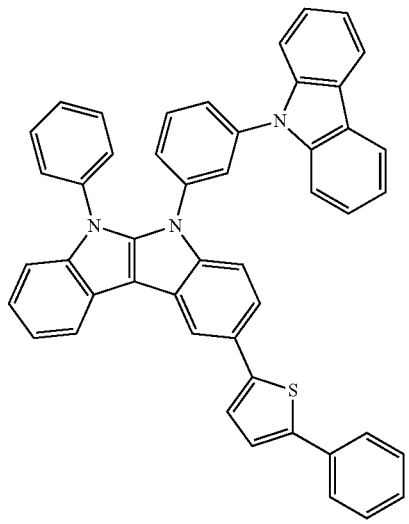
1-43
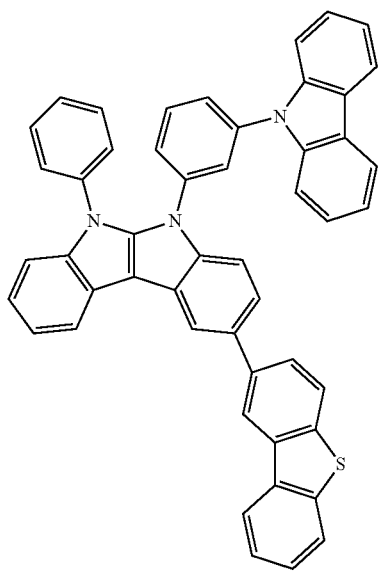
1-45
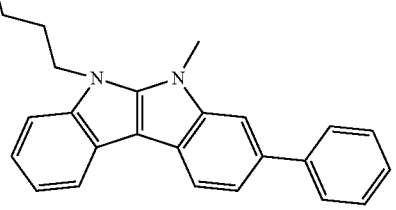
1-46
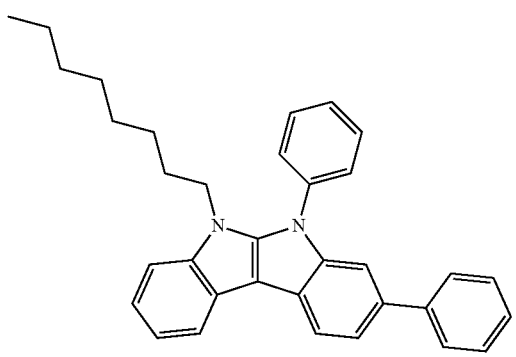
1-47
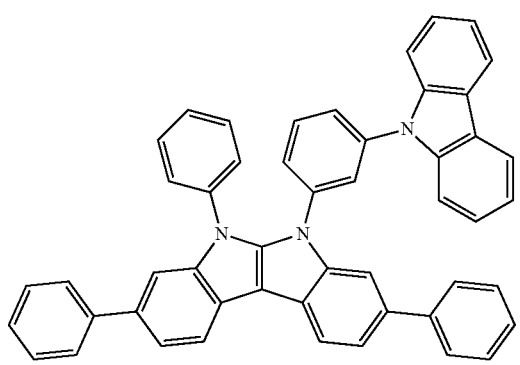

1-48
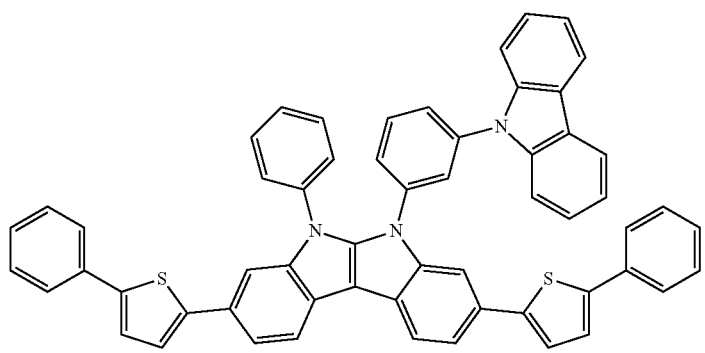
1-49
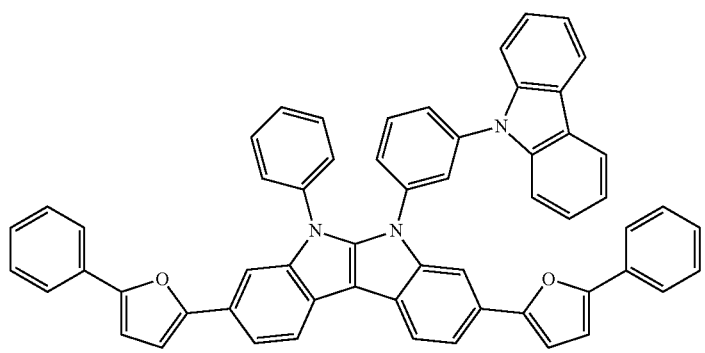
1-50
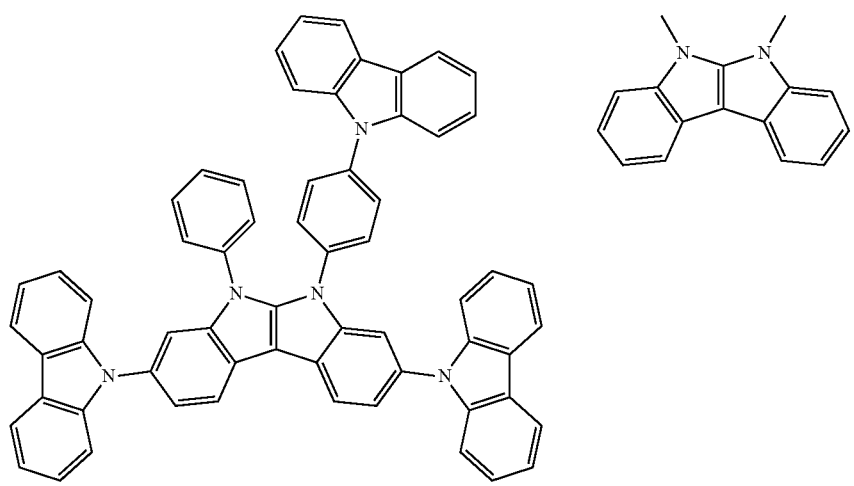
1-52

-continued
1-53
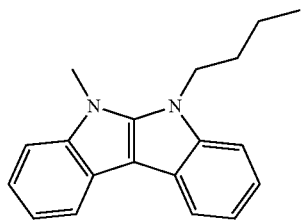
1-54
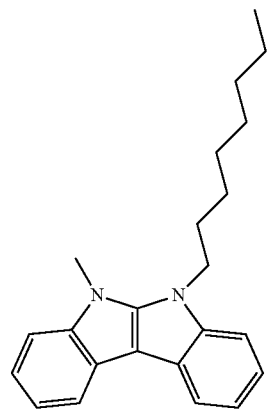
1-55
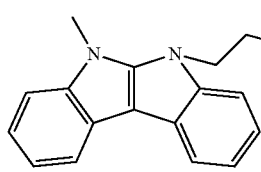
1-56
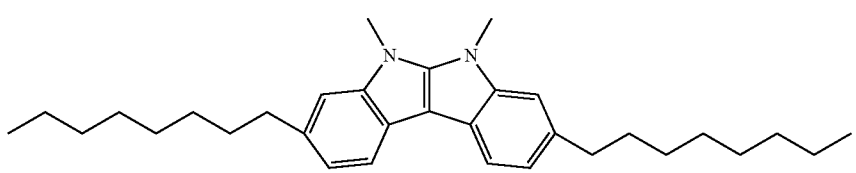
1-57
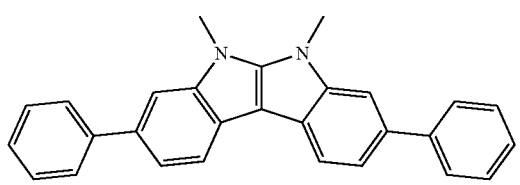
1-58
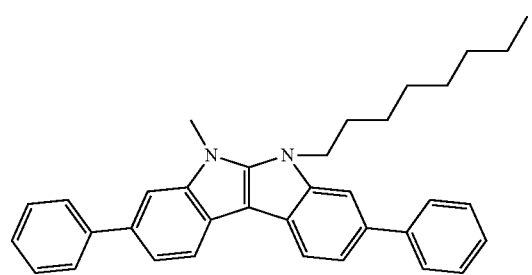
1-59
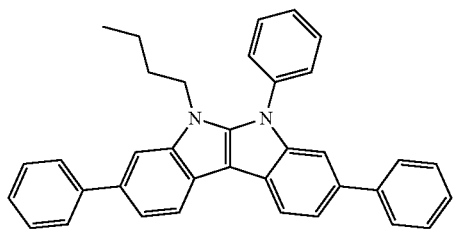
1-60
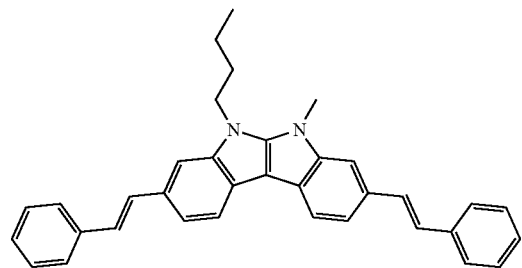

1-61
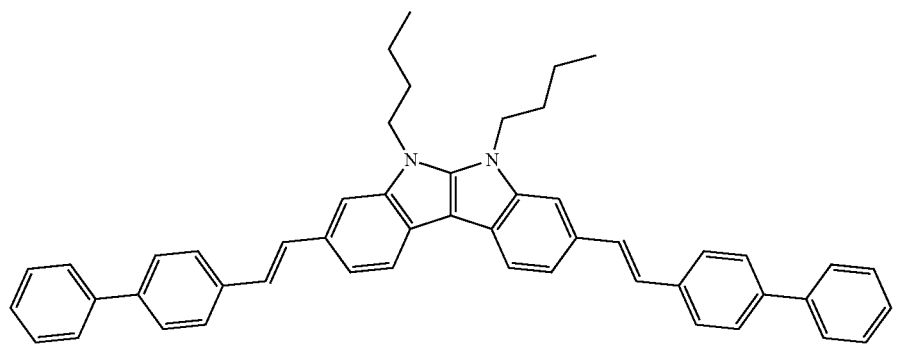
1-62
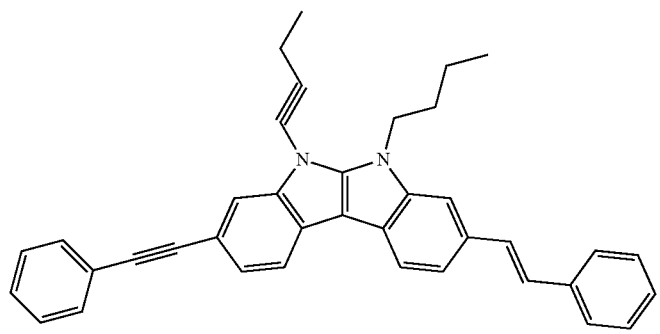
1-63
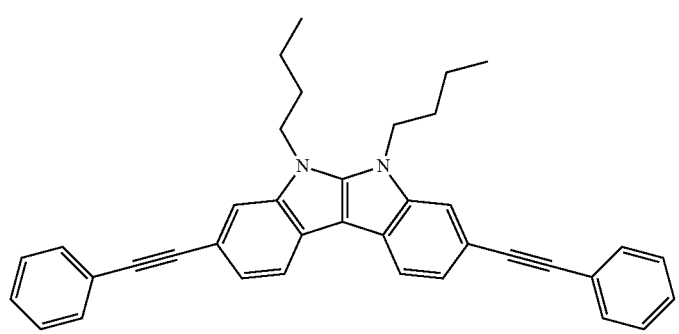

1-64
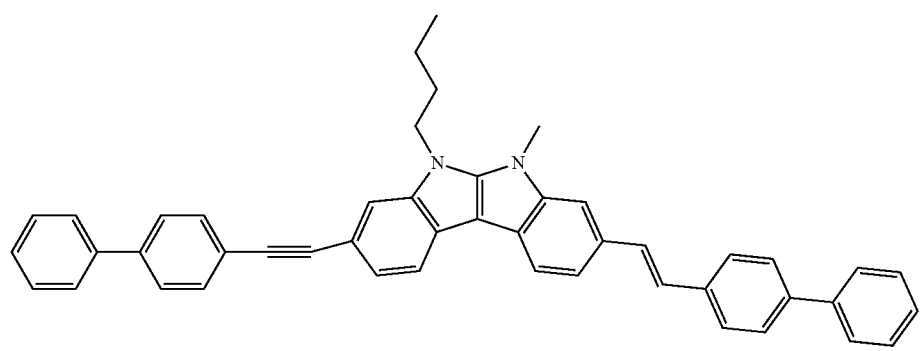
1-65
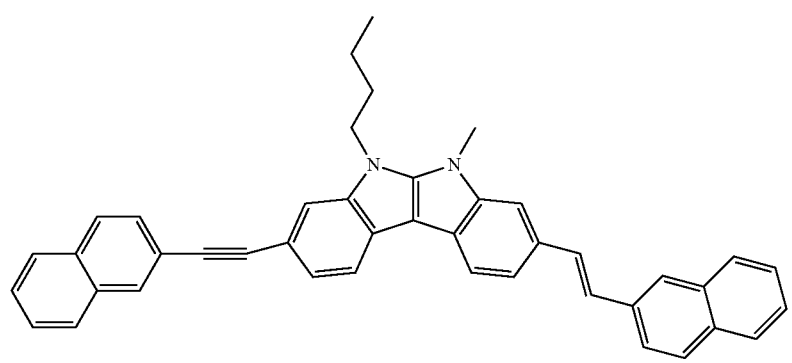
1-66
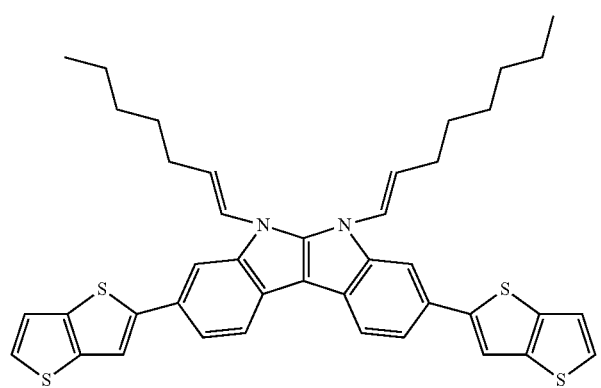

-continued
1-67
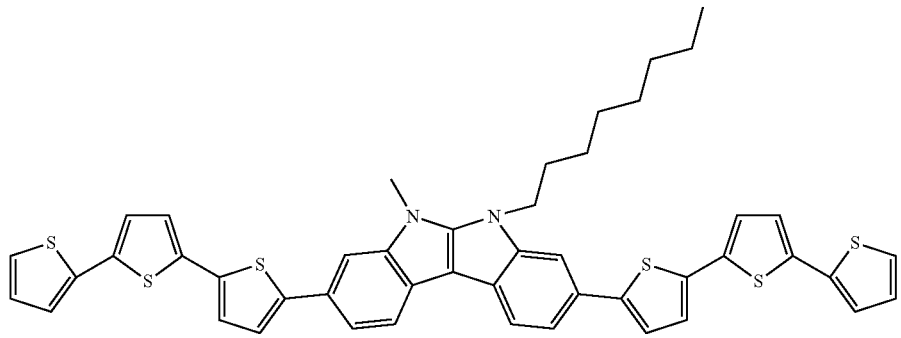
1-68
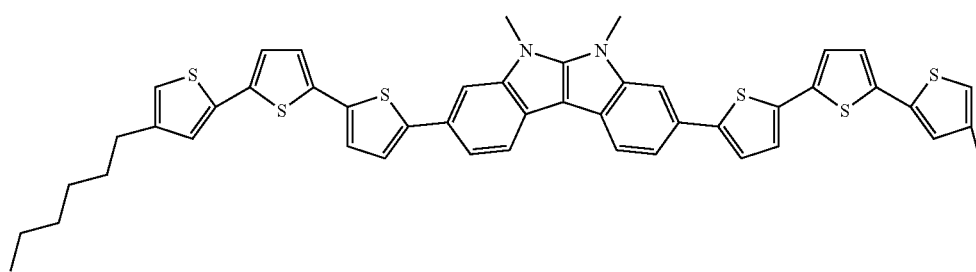
1-69
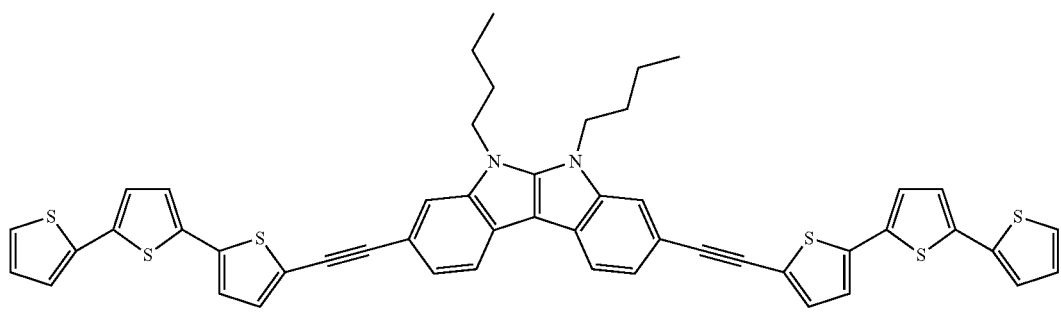
1-70
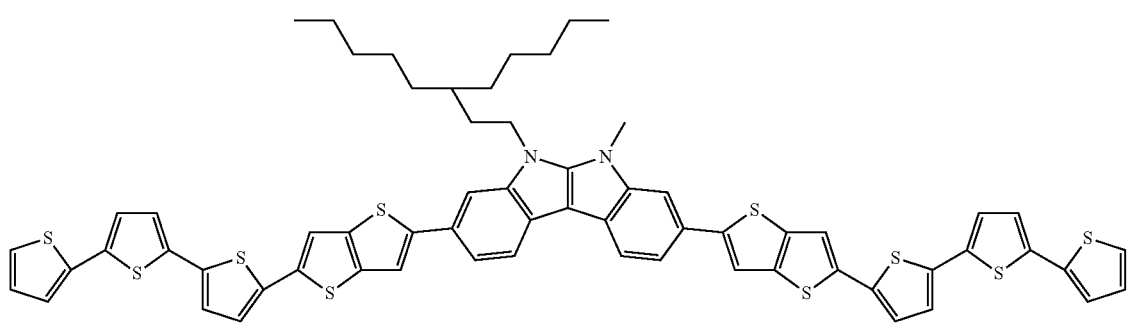
2-1
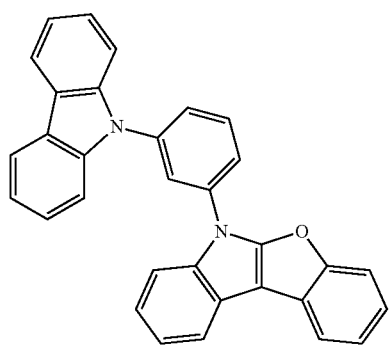
2-2
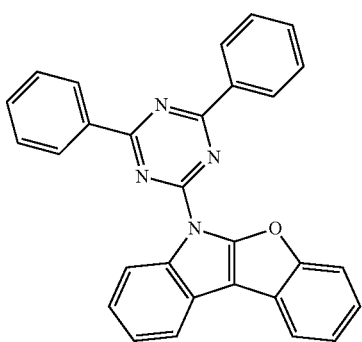

-continued
2-3
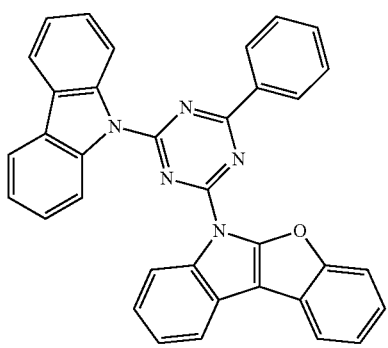
2-4
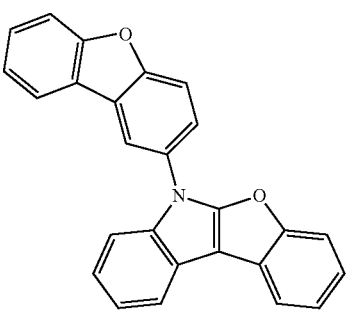
2-5
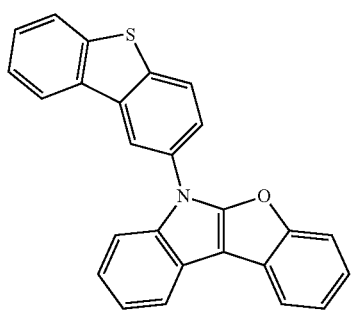
2-6
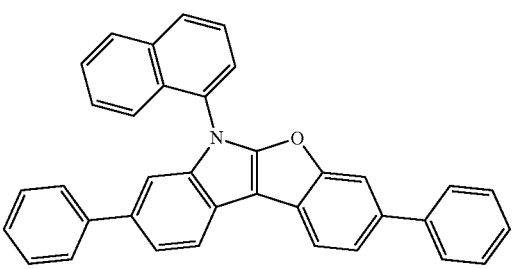
2-7
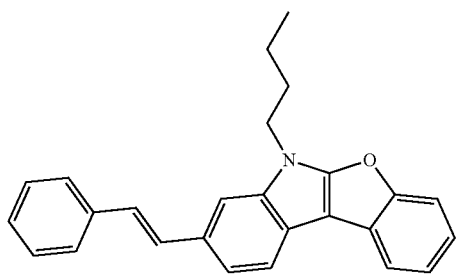
2-8
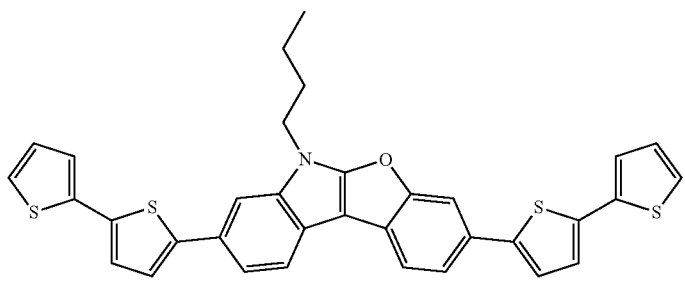

-continued
3-1
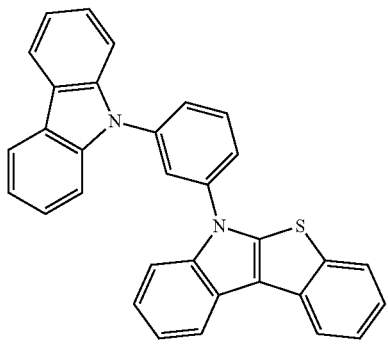
3-2
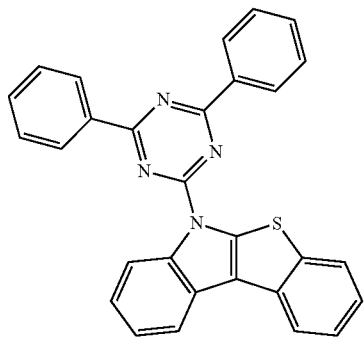
3-3
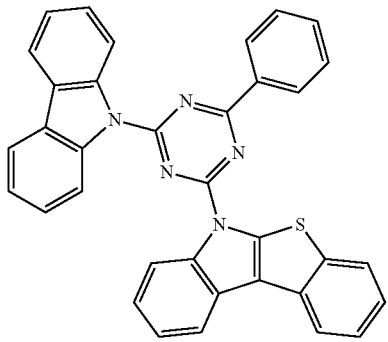
3-4
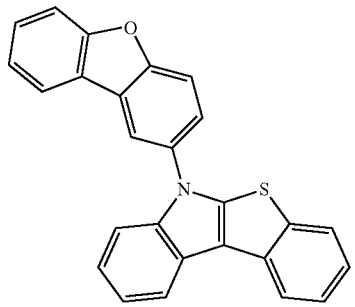
3-5
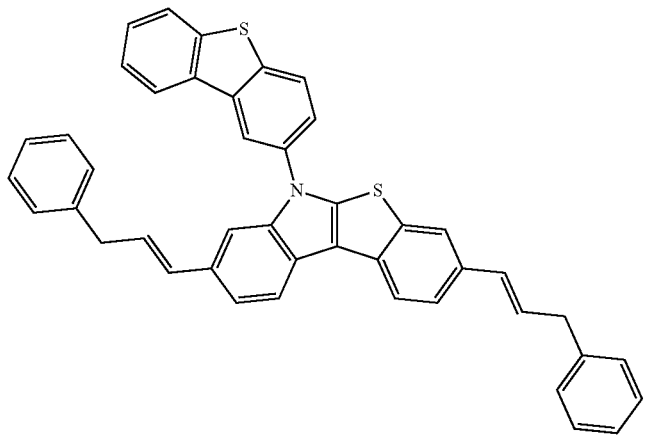
3-6
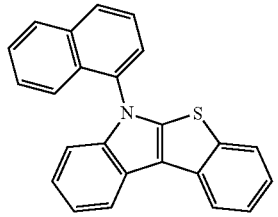
4-1
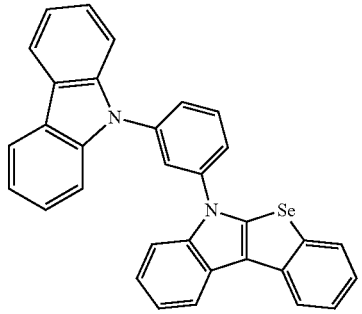

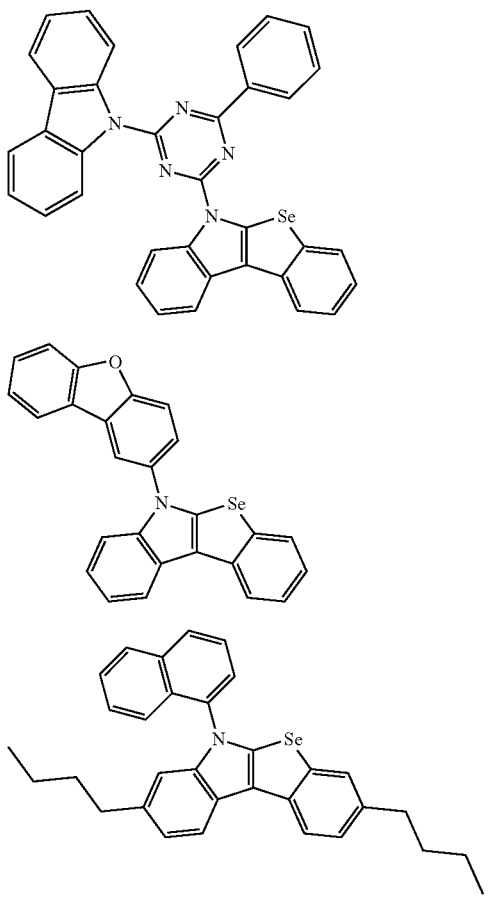

An organic semiconductor material and an organic electronic device according to this invention are explained hereinafter. As the nitrogen-containing aromatic compound of this invention itself has a function of an organic semiconductor material, it is useful as an organic semiconductor material. The organic semiconductor material of this invention contains the nitrogen-containing aromatic compound of this invention. The organic semiconductor material of this invention performs satisfactorily so long as it contains the nitrogen-containing aromatic compound of this invention. Hence, the organic semiconductor material of this invention may be used as a mixture with other organic semiconductor materials or it may contain a variety of dopants. For example, in the case where the organic semiconductor material of this invention is used in the light-emitting layer of an organic EL device, derivatives of coumarin, quinacridone, rubrene, and stilbene, fluorescent dyes, and noble metal complexes such as iridium complexes and platinum complexes may be used as dopants.

The organic electronic device of this invention is an electronic device using the organic semiconductor material of this invention; that is, the organic electronic device of this invention contains the nitrogen-containing aromatic compound of this invention. Concretely, the organic electronic device of this invention comprises organic layers and at least one of the organic layers contains the compound of this invention.

The organic electronic device of this invention can be constructed in a variety of modes and one of the suitable modes is an organic EL device. Concretely, an organic EL device is an organic electronic device in which an anode, organic layers containing a light-emitting layer, and a cathode are piled one upon another on a substrate and the said organic layers contain the compound of this invention.

The structure of the organic EL device of this invention is explained hereinafter with reference to the drawing, but it will not be limited to the one illustrated in the drawing.

FIG. 1 is a cross section illustrating an example of the structure of an organic EL device generally used in this invention and the numbers in FIG. 1 stand for the following: 1 for a substrate, 2 for an anode, 3 for a hole-injecting layer, 4 for a hole-transporting layer, 5 for a light-emitting layer, 6 for an electron-transporting layer, and 7 for a cathode. The organic EL device of this invention may further comprise an exciton-blocking layer adjacent to the light-emitting layer or an electron-blocking layer between the light-emitting layer and the hole-injecting layer. The exciton-blocking layer may be inserted either on the anode side or on the cathode side of the light-emitting layer or may be inserted simultaneously on both sides. The organic EL device of this invention comprises the substrate, the anode, the light-emitting layer, and the cathode as essential layers. However, it is preferable that the device comprises a hole-injecting/transporting layer and an electron-injecting/transporting layer in addition to the essential layers and further comprises a hole-blocking layer between the light-emitting layer and the electron-injecting/transporting layer. The hole-injecting/transporting layer means a hole-injecting layer and/or a hole-transporting layer while the electron-injecting/transporting layer means an electron-injecting layer and/or an electron-transporting layer.

The organic EL device of this invention can be so constructed as to have a structure that is the reverse of the structure illustrated in FIG. 1 by piling the cathode 7, the electron-transporting layer 6, the light-emitting layer 5, the hole-transporting layer 4, and the anode 2 one upon another in this order on the substrate 1. In this case, it is possible to add or omit a layer or layers according to the need.

The compound of this invention can be used in any of the layers in the organic EL device. The compound is used preferably in the light-emitting layer, hole-transporting layer, electron-blocking layer, hole-blocking layer, or electron-transporting layer and it is used particularly preferably in the light-emitting layer, hole-transporting layer, or electron-blocking layer.

—Substrate—

The organic EL device of this invention is preferably supported by a substrate. There is no specific restriction on the substrate and any of the substrates that have been used customarily in organic EL devices can be used. A substrate made from a material such as glass, transparent plastic, and quartz may be used.

—Anode—

The anode of an organic EL device is preferably made from an electrode substance having a high work function (4 eV or more) such as a metal, an alloy, an electrically conductive compound, and a mixture thereof. Specific examples of the electrode substances of this kind include metals such as Au and electrically conductive transparent materials such as CuI, indium tin oxide (ITO), $SnO_2$, and ZnO. Further, a material such as IDIXO ($In_2O_3$—ZnO) that is amorphous and formable into a transparent electrically conductive film may be used. The anode may be formed by preparing a thin film from any of these electrode substances by a method such as vapor deposition and sputtering and then forming a pattern of desired shape on the thin film by photolithography. Or, in the case where high accuracy is not required in patterning (100 μm or more), a pattern may be formed through a mask of desired shape during vapor deposition or sputtering of the aforementioned electrode substance. In the case where a substance that is applicable by a coating method such as an electrically conductive organic compound is used, a wet film-forming process such as printing and coating may be employed. When emitted light is taken out from the anode, the transmittance is desirably set at 10% or more and the sheet resistance as the anode is preferably several hundred Ω/□ or less. Further, the thickness of the film is normally selected from the range of 10 to 1,000 nm, preferably 10 to 200 nm, although it varies with the film-forming material.

—Cathode—

Meanwhile, the cathode is made from an electrode substance having a low work function (4 eV or less) such as a metal (hereinafter referred to as electron-injecting metal), an alloy, an electrically conductive compound, and a mixture thereof. Specific examples of the electrode substances of this kind include sodium, a sodium-potassium alloy, magnesium, lithium, a magnesium/copper mixture, a magnesium/silver mixture, a magnesium/aluminum mixture, a magnesium/indium mixture, an aluminum/aluminum oxide ($Al_2O_3$) mixture, indium, a lithium/aluminum mixture, and a rare earth metal. Of the aforementioned substances, a mixture of an electron-injecting metal and a second metal that is higher in work function and more stable than the electron-injecting metal is suitable for use as an electrode substance from the viewpoint of electron-injecting property and durability against oxidation and the like. Examples include a magnesium/silver mixture, a magnesium/aluminum mixture, a magnesium/indium mixture, an aluminum/aluminum oxide ($Al_2O_3$) mixture, a lithium/aluminum mixture, and aluminum. The cathode is formed by preparing a thin film from any of these electrode substances by a method such as vapor deposition and sputtering. The sheet resistance as the cathode is preferably several hundred Ω/□ or less and the thickness of the film is selected from the range of 10 nm to 5 μm, preferably in the range of 50 to 200 nm. Making either the anode or the cathode of an organic EL device transparent or translucent to allow transmission of emitted light advantageously improves the luminance.

A transparent or translucent cathode may be made by forming a cathode with a film thickness of 1 to 20 nm from the aforementioned metal and then forming thereon a film of one of the electrically conductive transparent materials described above in explanation of the anode. This method can be applied to the fabrication of a device in which both the anode and the cathode have good light-transmitting properties.

—Light-Emitting Layer—

The light-emitting layer may be either a fluorescent light-emitting layer or a phosphorescent light-emitting layer, preferably a phosphorescent light-emitting layer.

In the case where the light-emitting layer is a fluorescent light-emitting layer, at least one kind of fluorescent light-emitting material may be used singly, but it is preferable to use a fluorescent light-emitting material as a fluorescent dopant and incorporate a host material in the layer.

A compound represented by general formula (1) may be used as a fluorescent light-emitting material in the light-emitting layer. In the case where the said compound is used in any of the organic layers other than the light-emitting layer, a suitable material is selected from fluorescent light-emitting materials that are known in a large number of patent documents and elsewhere and used instead. Examples of such fluorescent light-emitting materials include benzoxazole derivatives, benzimidazole derivatives, benzothiazole derivatives, styrylbenzene derivatives, polyphenyl derivatives, diphenylbutadiene derivatives, tetraphenylbutadiene derivatives, naphthalimide derivatives, coumarin derivatives, fused aromatic compounds, perinone derivatives, oxadiazole derivatives, oxazine derivatives, aldazine derivatives, pyrrolidine derivatives, cyclopentadiene derivatives, bis styrylanthracene derivatives, quinacridone derivatives, pyrrolopyridine derivatives, thiadiazolopyridine derivatives, styrylamine derivatives, diketopyrrolopyrrole derivatives, aromatic dimethylidene-based compounds, a variety of metal complexes represented by metal complexes of 8-quinolinol derivatives, metal complexes of pyrromethene derivatives, rare earth metal complexes, and transition metal complexes, polymer compounds such as polythiophene, polyphenylene, and polyphenylenevinylene, and organic silane derivatives. Preferable examples include fused aromatic compounds, styryl compounds, diketopyrrolopyrrole compounds, oxazine compounds, pyrromethene metal complexes, transition metal complexes, lanthanoid complexes. More preferable examples include naphthacene, pyrene, chrysene, triphenylene, benzo[c]phenanthrene, benzo[a]anthracene, pentacene, perylene, fluoranthene, acenaphthofluoranthene, dibenzo[a,j]anthracene, dibenzo[a,h]anthracene, benzo[a]naphthacene, hexacene, anthanthrene, naphtho[2,1-f]isoquinoline, α-naphthaphenanthridine, phenanthroxazole, quinolino[6,5-f]quinoline, and benzothiophanthrene. These compounds may be substituted with an aryl group, an aromatic heterocyclic group, a diarylamino group, or an alkyl group.

In the case where one of the aforementioned fluorescent light-emitting materials is used as a fluorescent dopant and a host material is incorporated, the content of the fluorescent dopant in the light-emitting layer is in the range of 0.01 to 20 wt %, preferably in the range of 0.1 to 10 wt %.

An organic EL device normally emits light when electric charges are injected into a light-emitting material from both the anode and the cathode and the light-emitting material is raised to an excited state. It is said that, in the case of a charge injection type organic EL device, 25% of the excitons thus generated is in the excited singlet state while the remaining 75% of the excitons is in the excited triplet state. As reported in the Preprints of the 57th United Lecture Meeting of the Japan Society of Applied Physics (19p-ZK-4 and 19p-ZK-5), a specified fluorescent light-emitting substance is known to manifest thermally activated delayed fluorescence as the energy of the substance once transferred to the excited triplet state by intersystem crossing or the like returns to the excited singlet state by inverse intersystem crossing caused by triplet-triplet annihilation or absorption of thermal energy and radiates fluorescence. An organic EL device in which the compound of this invention is used can also manifest delayed fluorescence. In this case, both fluorescence and delayed fluorescence may be involved. However, it is allowable that a part of emitted light comes from the host material.

In the case where the light-emitting layer is a phosphorescent light-emitting layer, the layer in question contains a phosphorescent dopant and a host material. An organic metal complex containing at least one metal selected from ruthenium, rhodium, palladium, silver, rhenium, osmium, iridium, platinum, and gold is preferably used as a phosphorescent dopant material. Organic metal complexes of this kind are known in the aforementioned prior art technical documents and elsewhere and a suitable material may be selected from them and used.

Preferred phosphorescent dopants include complexes containing a noble metal element such as Ir in the center, typically Ir(ppy)$_3$, complexes such as (Bt)$_2$Iracac, and complexes such as (Btp)Ptacac. Specific examples of these complexes are illustrated below, but are not limited thereto.

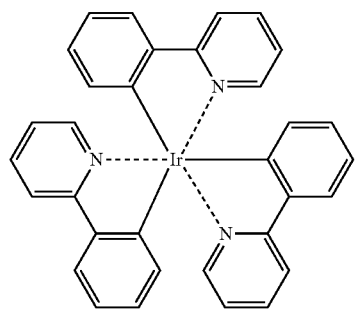

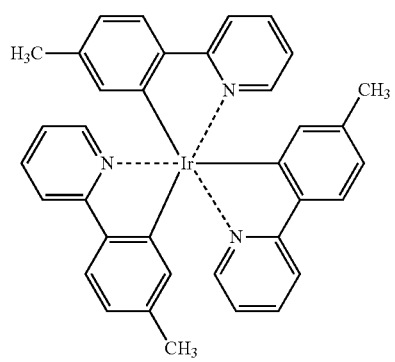

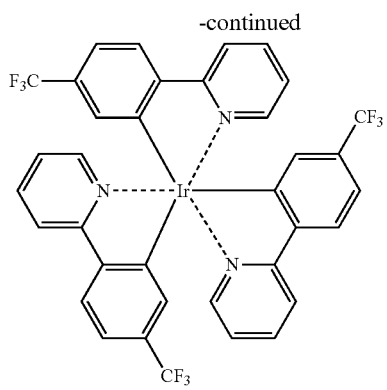

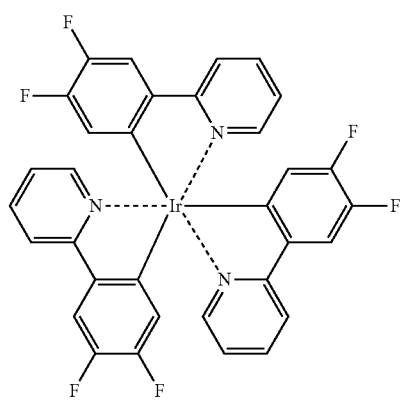

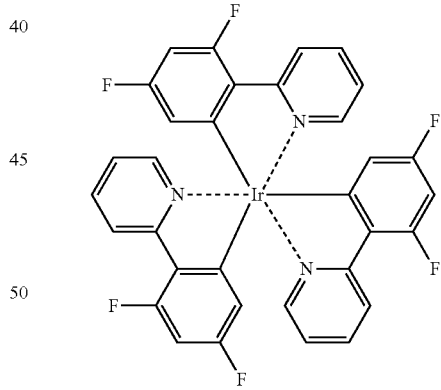

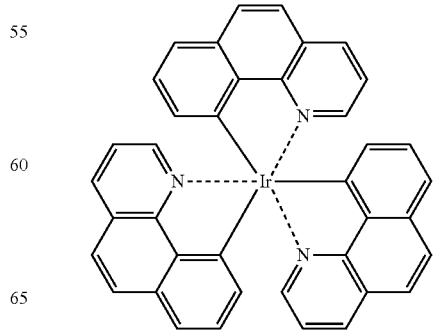

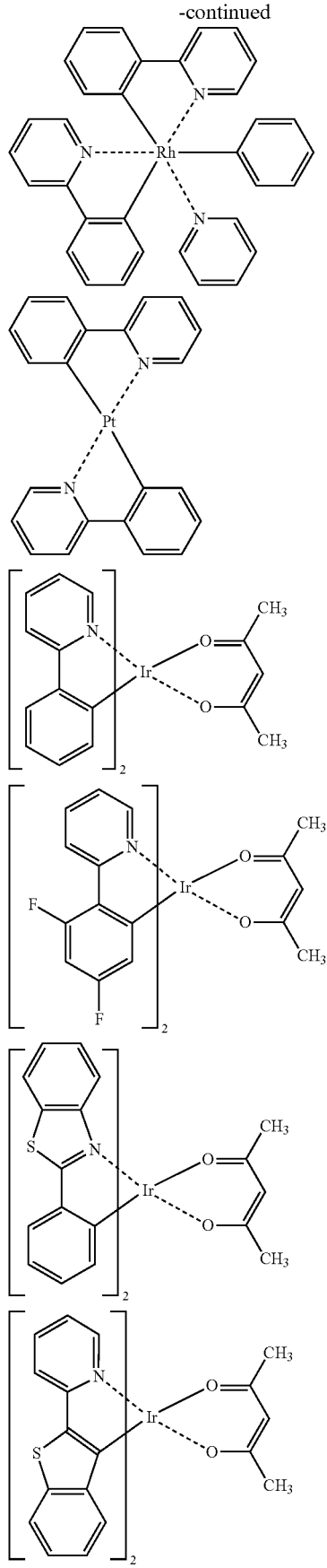
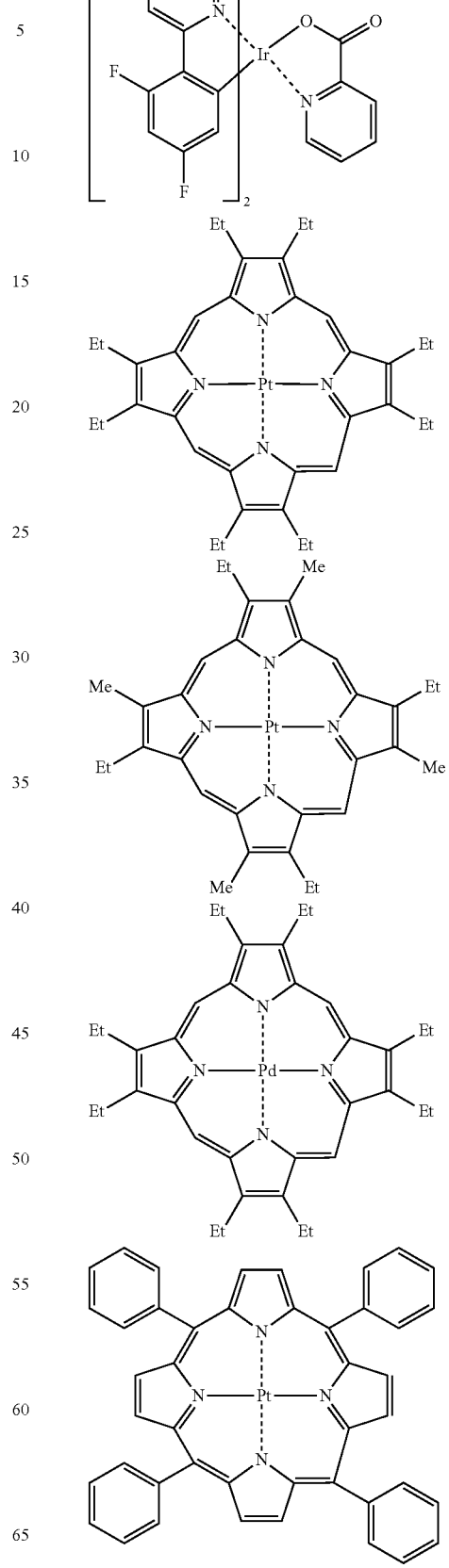

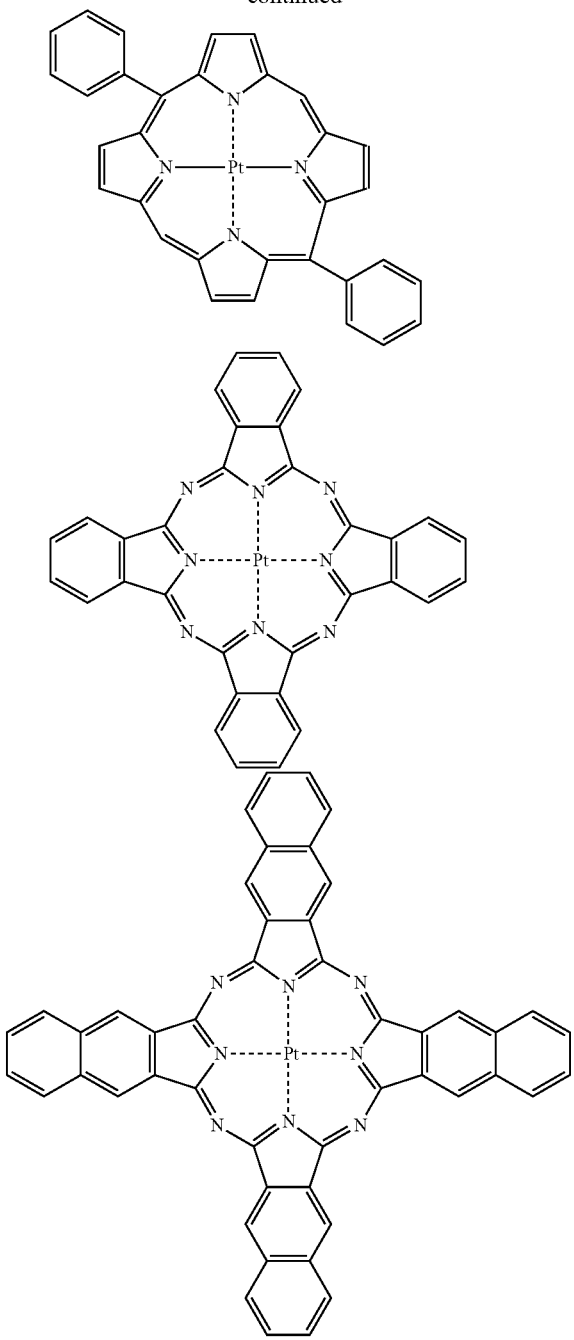

The content of the aforementioned phosphorescent dopant in the light-emitting layer is in the range of 1 to 50 wt %, preferably in the range of 5 to 30 wt %.

It is preferable to use the compound of this invention represented by the aforementioned general formula (1) as a host material in the light-emitting layer. However, in the case where the said compound is used in any of the organic layers other than the light-emitting layer, a host material other than the compound of this invention may be used in the light-emitting layer. Further, the compound of this invention may be used together with other host material. Still further, plural kinds of known host materials may be used together.

Of the known host compounds, those suitable for use preferably have a hole transport ability or an electron transport ability, can prevent the wavelength of emitted light from shifting to longer wavelengths, and have a high glass transition temperature.

These host materials are described in a large number of patent documents and elsewhere and a suitable material may be selected from them. Specific examples include, but are not limited to, indole derivatives, carbazole derivatives, indolocarbazole derivatives, triazole derivatives, oxazole derivatives, oxadiazole derivatives, imidazole derivatives, polyaryalkane derivatives, pyrazoline derivatives, pyrazolone derivatives, phenylenediamine derivatives, arylamine derivatives, amino-substituted chalcone derivatives, styrylanthracene derivatives, fluorenone derivatives, hydrazone derivatives, stilbene derivatives, silazane derivatives, aromatic tertiary amine compounds, styrylamine compounds, aromatic dimethylidene-based compounds, porphyrin-based compounds, anthraquinodimethan derivatives, anthrone derivatives, diphenylquinone derivatives, thiopyran dioxide derivatives, heterocyclic tetracarboxylic acid anhydrides of naphthalene and perylene, a variety of metal complexes represented by metal complexes of phthalocyanine derivatives and 8-quinolinol derivatives, metal phthalocyanines, and metal complexes of benzoxazole derivatives and benzothiazole derivatives, and polymer compounds such as polysilane-based compounds, poly(N-vinylcarbazole) derivatives, aniline-based copolymers, thiophene oligomers, polythiophene derivatives, polyphenylene derivatives, polyphenylenevinylene derivatives, and polyfluorene derivatives.

—Injecting Layer—

The injecting layer is a layer that is provided between an electrode and an organic layer to reduce the driving voltage and improve the luminance. The injecting layer includes a hole-injecting layer and an electron-injecting layer and may be provided respectively between the anode and the light-emitting layer or the hole-transporting layer and between the cathode and the light-emitting layer or the electron-transporting layer. The injecting layer may be provided according to the need. The compound of this invention represented by general formula (1) may be used as a material for the injecting layer. However, in the case where the said compound is used in any of the organic layers other than the injecting layer, a suitable compound is selected from the known compounds and used.

—Hole-Blocking Layer—

The hole-blocking layer has a function of the electron-transporting layer in a broad sense and is composed of a hole-blocking material that has an extremely poor ability to transport holes while having a function of transporting electrons. The hole-blocking layer can improve the probability of recombination of electrons and holes by transporting electrons while blocking holes.

The compound of this invention represented by general formula (1) may be used in the hole-blocking layer. However, in the case where the said compound is used in any of the organic layers other than the hole-blocking layer, a known hole-blocking material may be used instead. Further, any of the materials for the electron-transporting layer to be described later on may be used as a hole-blocking material according to the need.

—Electron-Blocking Layer—

The electron-blocking layer is made from a material that has an extremely poor ability to transport electrons while having a function of transporting holes and it can improve the probability of recombination of electrons and holes by transporting holes while blocking electrons.

As a material for the electron-blocking layer, the compound of this invention represented by the aforementioned general formula (1) is preferably used. However, in the case where the said compound is used in any of the organic layers other than the electron-blocking layer, any of the materials for the hole-transporting layer to be described later on may be used instead according to the need. The thickness of the electron-blocking layer is preferably 3 to 100 nm, more preferably 5 to 30 nm.

—Exciton-Blocking Layer—

The exciton-blocking layer is a layer for preventing the excitons that are generated by recombination of holes and electrons in the light-emitting layer from diffusing to the charge-transporting layer. The insertion of this layer makes it possible to efficiently confine excitons in the light-emitting layer and enhance the luminous efficiency of the device. The exciton-blocking layer may be inserted either on the anode side or on the cathode side adjacent to the light-emitting layer or simultaneously on both the anode and the cathode sides.

The compound of this invention represented by general formula (1) may be used as a material for the exciton-blocking layer. However, in the case where the said compound is used in any of the organic layers other than the exciton-blocking layer, a suitable material is selected from the known compounds such as 1,3-dicarbazolylbenzene (mCP) and bis(2-methyl-8-quinolinolato)-4-phenylphenolatoaluminum (III) (BAlq) and used.

—Hole-Transporting Layer—

The hole-transporting layer is made from a hole-transporting material that has a function of transporting holes and it may be provided in a single layer or a plurality of layers.

The hole-transporting material has either a property of injecting or transporting holes or a property of constituting a barrier to electrons and it may be an organic substance or an inorganic substance. The compound of this invention represented by general formula (1) is preferably used in the hole-transporting layer. However, in the case where the said compound is used in any of the organic layers other than the hole-transporting layer, a suitable material may be selected from the known compounds and used. Specific examples of these known hole-transporting materials that are suitable for use include triazole derivatives, oxadiazole derivatives, imidazole derivatives, polyarylalkane derivatives, pyrazoline derivatives, pyrazolone derivatives, phenylenediamine derivatives, aromatic amine derivatives, amino-substituted chalcone derivatives, oxazole derivatives, styrylanthracene derivatives, fluorenone derivatives, hydrazone derivatives, stilbene derivatives, silazane derivatives, aniline-based copolymers, porphyrin compounds, styrylamine compounds, and electrically conductive oligomers, particularly thiophene oligomers. Preferable examples include porphyrin compounds, aromatic tertiary amine compounds, and styrylamine compounds and more preferable examples include aromatic tertiary amine compounds.

—Electron-Transporting Layer—

The electron-transporting layer is made from a material that has a function of transporting electrons and may be provided in a single layer or a plurality of layers.

An electron-transporting material (serving also as a hole-blocking material in some cases) may be an arbitrary material so long as it has a function of transporting electrons that are injected from the cathode to the light-emitting layer. The compound of this invention represented by general formula (1) may be used in the electron-transporting layer. However, in the case where the said compound is used in any of the organic layers other than the electron-transporting layer, a suitable material may be selected from the known compounds and used. Examples of such known compounds include nitro-substituted fluorene derivatives, diphenylquinone derivatives, thiopyran dioxide derivatives, carbodiimide, fluorenylidenemethane derivatives, anthraquinodimethan derivatives, anthrone derivatives, and oxadiazole derivatives. Further, thiadiazole derivatives that are derived from the aforementioned oxadiazole derivatives by substituting a sulfur atom for the oxygen atom of the oxadiazole ring and quinoxaline derivatives that have a quinoxaline ring known as an electron-withdrawing group may be used as electron-transporting materials. Further, polymer materials that contain any of these materials in the polymer chain or polymer materials whose backbone is constituted of any of these materials may be used.

An organic TFT device is another suitable mode of organic electronic devices containing the compound of this invention. Concretely, an organic TFT device is an organic electronic device consisting of a gate electrode, a gate insulator layer, an organic semiconductor layer, and a source electrode and a drain electrode stacked on a substrate and the organic semiconductor layer contains the compound of this invention.

The structure of an organic TFT device according to this invention is explained hereinafter with reference to the drawings, but it is not limited to that illustrated in the drawings.

Figure 2:
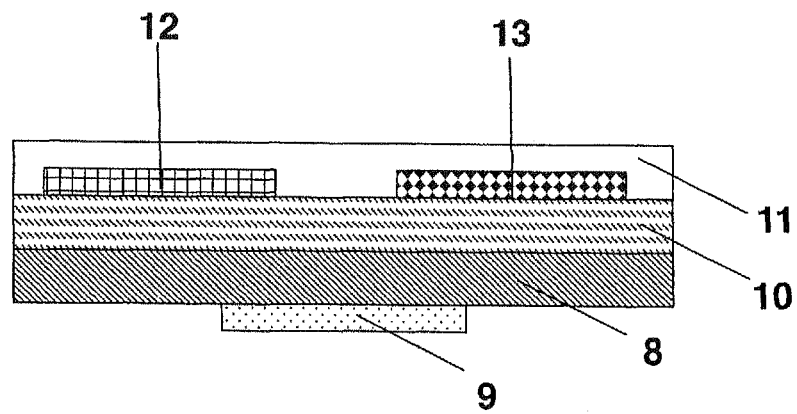
FIG. 2 is a schematic cross section illustrating an example of the structure of an organic TFT device.
Figure 3:
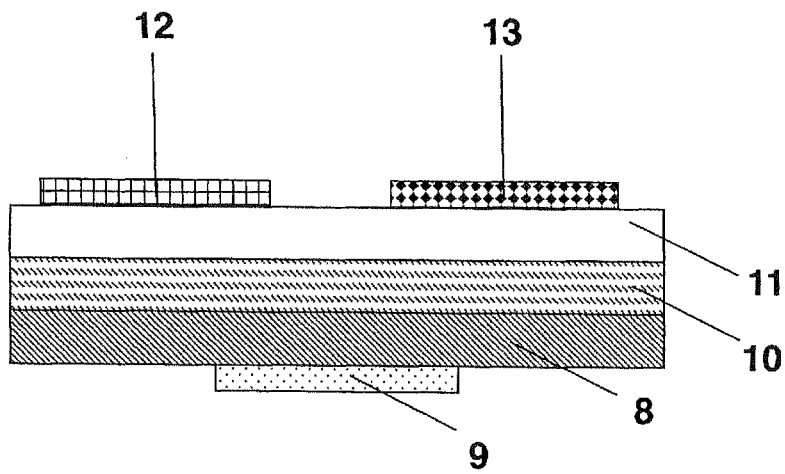
FIG. 3 is a schematic cross section illustrating another example of the structure of an organic TFT device.

FIGS. 2 and 3 each is a cross section illustrating an example of the structure of an organic TFT device and the numbers therein stand for the following; 8 for a substrate, 9 for a gate electrode, 10 for an insulator layer, 11 for an organic semiconductor layer, 12 for a source electrode, and 13 for a drain electrode.

—Substrate—

The substrate is not especially limited and it may be constructed in the well-known manner from a material such as glass (for example, quartz glass), silicon, ceramics, and plastics. For example, a plastic substrate is made from all-purpose plastics such as polyethylene terephthalate, polyethylene naphthalate, and polycarbonate. A plastic substrate is preferably laminated to a gas barrier film to reduce transmission of gases such as oxygen and moisture vapor.

—Gate Electrode—

The gate electrode is not especially limited and it may be constructed in the well-known manner. Materials useful for construction of a gate electrode include metals such as gold, platinum, chromium, tungsten, tantalum, nickel, copper, aluminum, silver, magnesium, and calcium, alloys thereof, polysilicon, amorphous silicon, graphite, ITO, zinc oxide, and electrically conductive polymers.

—Gate Insulation Layer—

The gate insulation layer is not especially limited and it may be constructed in the well-known manner. The gate insulation layer is made from a material such as $SiO_2$, $Si_3N_4$, SiON, $Al_2O_3$, $Ta_2O_5$, amorphous silicon, polyimide resin, polyvinylphenol resin, polyparaxylene resin, polymethyl methacrylate resin, and fluororesin (PTFE, PFA, ETFE, PCTFE, CYTOP (registered trademark), etc.).

—Organic Semiconductor Layer—

The organic semiconductor layer is not especially limited so long as it contains the compound of this invention. For example, the organic semiconductor layer may substantially consists of the compound of this invention alone or it may additionally contain a material other than the compound of this invention.

—Source Electrode and Drain Electrode—

The source electrode and the drain electrode are not especially limited and they may be constructed in the well-known manner. The materials suitable for use in the source electrode and the drain electrode include metals such as gold, platinum, chromium, tungsten, tantalum, nickel, copper, aluminum, silver, magnesium, and calcium, alloys thereof, polysilicon, amorphous silicon, graphite, ITO, zinc oxide, and electrically conductive polymers.

The constituent layers of an organic TFT device may be stacked in the manner of either structure (i) in which a gate electrode, a gate insulation layer, an organic semiconductor layer, and source/drain electrodes are arranged in this order on a substrate or structure (ii) in which a gate electrode, a gate insulation layer, source/drain electrodes, and an organic semiconductor layer are arranged in this order on a substrate. The method for fabricating an organic TFT device is not especially limited. However, in the case of structure (i), a top contact method that consists of stacking a gate electrode, a gate insulation layer, an organic semiconductor layer, and source/drain electrodes in this order on a substrate is available. In the case of structure (ii), the bottom contact method that consists of stacking a gate electrode, a gate insulation layer, source/drain electrodes, and an organic semiconductor layer in this order on a substrate is available.

The method for forming a gate electrode, a gate insulation layer and source/drain electrodes is not especially limited and these electrodes can be made from the aforementioned materials by a known film-forming process such as vacuum deposition, electron beam deposition, RF sputtering, spin coating, and printing. The method for forming an organic semiconductor layer is not especially limited and this layer can be made from the compound of this invention or from an organic semiconductor material containing the compound of this invention by a known film-forming process such as vapor deposition, spin coating, inkjet coating, and printing.

An organic TFT device is not especially limited in its uses and, for example, it may be suitably used as a TFT device to drive pixels in flexible displays in which plastic substrates are used. It is generally difficult process-wise to form a TFT device constructed of an inorganic substance on a plastic substrate. However, since the fabrication of the organic electronic device of this invention that consists of an organic TFT device uses a process such as vacuum deposition, spin coating, inkjet printing, and printing, but not a high temperature process as described above, a TFT device for driving pixels can be formed on a plastic substrate. In particular, the compound of this invention allows application of a low-cost process such as spin coating, inkjet printing, and printing on account of its good solubility in an all-purpose organic solvent such as chloroform, tetrahydrofuran, and toluene and it is suited for manufacture of inexpensive paper-like (flexible) displays.

Still another suitable mode of organic electronic devices containing the compound of this invention is a photovoltaic device, preferably an organic thin film solar cell. Concretely, it is an organic electronic device comprising a positive electrode, an organic semiconductor layer, and a negative electrode arranged on a substrate and the said organic semiconductor layer contains the compound of this invention.

The structure of a photovoltaic device according to this invention is explained hereinafter with reference to the drawings, but it is not limited to those shown in the drawings.

Figure 4:
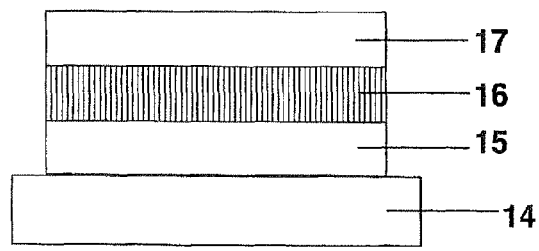
FIG. 4 is a schematic cross section illustrating an example of the structure of a photovoltaic device.
Figure 5:
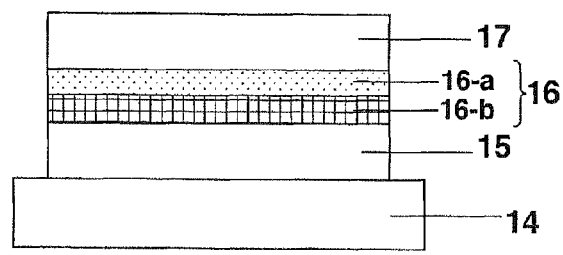
FIG. 5 is a schematic cross section illustrating another example of the structure of a photovoltaic device.

FIG. 4 is a cross section illustrating an example of the structure of a photovoltaic device generally used in this invention and the numbers therein stand for the following; 14 for a substrate, 15 for a positive electrode, 16 for an organic semiconductor, and 17 for a negative electrode. Further, FIG. 5 is a cross section illustrating an example of the structure of a photovoltaic device in which organic semiconductor layers are stacked; 16-a stands for an electron-donating organic semiconductor layer and 16-b for an electron-accepting organic semiconductor layer.

—Substrate—

The substrate is not especially limited and it may be constructed in the well-known manner. A substrate made from a material that is mechanically and thermally strong and transparent such as glass and a transparent resin film is preferably used. Examples of resins from which transparent films are made include polyethylene, ethylene-vinyl acetate copolymer, ethylene-vinyl alcohol copolymer, polypropylene, polystyrene, polymethyl methacrylate, polyvinyl chloride, polyvinyl alcohol, polyvinyl butyral, nylon, polyetheretherkeone, polysulfone, polyethersulfone, tetrafluorethylene-perfluoroalkyl vinyl ether copolymer, polyvinyl fluoride, tetrafluoroethylene-ethylene copolymer, tetrafluoroethylene-hexafluoropropylene copolymer, polychlorotrifluoroethylene, polyvinylidene fluoride, polyester, polycarbonate, polyurethane, polyimide, and polyetherimide.

—Electrodes—

As for electrode materials, it is preferable to use an electrically conductive material having a high work function for one electrode and an electrically conductive material having a low work function for the other electrode. The electrode that is made from an electrically conductive material having a high work function becomes a positive electrode. Preferable examples of electrically conductive materials having a high work function include metals such as gold, platinum, chromium, and nickel and transparent oxides and composite oxides of indium, tin, and the like such as indium tin oxide (ITO) and indium zinc oxide (IZO). Here, it is preferable that an electrically conductive material to be used as a positive electrode can be joined to the organic semiconductor layer by an ohmic contact. Furthermore, in the case where the hole-transporting layer to be described later on is used, it is preferable that an electrically conductive material to be used as a positive electrode can be joined to the hole-transporting layer by an ohmic contact.

The electrode that is made from an electrically conductive material having a low work function becomes a negative electrode. Examples of electrically conductive materials having a low work function include alkali metals and alkaline earth metals, specifically lithium, magnesium, and calcium. Tin, silver, and aluminum are also desirable materials. An electrode composed of an alloy or laminate of the aforementioned metals is also used. Further, the current taken out of the device can be improved by introducing a metal fluoride such as lithium fluoride and cesium fluoride into the interface of the negative electrode and the electron-transporting layer. The electrically conductive material to be used for the negative electrode here can preferably be joined to the organic semiconductor layer by an ohmic contact. Furthermore, in the case where the electron-transporting layer to be described later on is used, the electrically conductive material to be used for the negative electrode can preferably be joined to the electron-transporting layer by an ohmic contact as well.

—Organic Semiconductor Layer—

The organic semiconductor layer contains the compound of this invention; that is, it contains an electron-donating organic material containing the compound of this invention and an electron-accepting organic material. It is preferable that the electron-donating organic material and the electron-accepting organic material are mixed together and, further, they are either soluble in each other or phase-separated on a molecular level. The size of domains in this phase-separated structure is not especially limited and it ranges normally from 1 nm to 50 nm. In the case where the electron-donating organic material and the electron-accepting organic layer are stacked, it is preferable that the layer containing the electron-donating organic material that exhibits the characteristics of a p-type semiconductor is on the side of the positive electrode and the layer containing the electron-accepting organic layer that exhibits the characteristics of an n-type semiconductor is on the side of the negative electrode. The thickness of the organic semiconductor layer is preferably in the range of 5 to 500 nm, more preferably in the range of 30 to 300 nm. In the case of stacked layers, the layer containing the electron-donating organic material of this invention accounts for a thickness of preferably 1 to 400 nm, more preferably 15 to 150 nm, of the aforementioned range.

The electron-donating organic material may consist of the compound of this invention represented by general formula (1) alone or may further contain other electron-donating organic materials. Examples of such other electron-donating organic materials include conjugated polymers such as polythiophene-based polymers, benzothiadiazole-thiophene-based derivatives, benzothiadiazole-thiophene-based copolymers, poly(p-phenylenevinylene)-based polymers, poly(p-phenylene)-based polymers, polyfluorene-based polymers, polypyrrole-based polymers, polyaniline-based polymers, polyacetylene-based polymers, and polythienylenevinylene-based polymers, phthalocyanine derivatives such as H2-phthalocyanine (H2Pc), copper phthalocyanine (CuPc), and zinc phthalocyanine (ZnPc), porphyrin derivatives, triarylamine derivatives such as N,N'-diphenyl-N,N'-di(3-methylphenyl)-4,4'-diphenyl-1,1'-diamine (TPD) and N,N'-dinaphthyl-N,N'-diphenyl-4,4'-diphenyl-1,1'-diamine (NPD), carbazole derivatives such as 4,4'-di(carbazol-9-yl)biphenyl (CBP), and low-molecular-weight organic compounds such as oligothiophene derivatives (terthiophene, quaterthiophene, sexithiophene, octithiophene, etc.).

As the compound of this invention represented by the aforementioned general formula (1) is electron-donating (exhibiting the characteristics of a p-type semiconductor), it is preferable for the photovoltaic device of this invention to contain additionally an electron-accepting organic material (an n-type organic semiconductor). Combination of the compound of this invention and an electron-accepting organic material can enhance the photovoltaic conversion efficiency of a photovoltaic device.

The electron-accepting organic materials suitable for use in the photovoltaic device of this invention are organic materials that exhibit the characteristics of an n-type semiconductor and examples include 1,4,5,8-naphthalenetetracarboxylic dianhydride (NTCDA), 3,4,9,10-perylenetetracarboxylic dianhydride (PTCDA), 3,4,9,10-perylenetetracarboxylic bis-benzimidazole (PTCBI), N,N'-dioctyl-3,4,9,10-naphtyltetracarboxydiimide (PTCDI-C8H), oxadiazole derivatives such as 2-(4-biphenylyl)-5-(4-t-butylphenyl)-1,3,4-oxadiazole (PBD) and 2,5-di(1-naphthyl)-1,3,4-oxadiazole (BND), triazole derivatives such as 3-(4-biphenylyl)-4-phenyl-5-(4-t-butylphenyl)-1,2,4-triazole (TAZ), phenanthroline derivatives, phosphine oxide derivatives, fullerene compounds (unsubstituted fullerenes such as C60, C70, C76, C78, C82, C84, C90, and C94 and substituted fullerenes such as [6,6]-phenyl C61 butyric acid methyl ester ([6,6]-PCBM), [5,6]-phenyl C61 butyric acid methyl ester ([5,6]-PCBM), [6,6]-phenyl C61 butyric acid hexyl ester ([6,6]-PCBH), [6,6]-phenyl C61 butyric acid dodecyl ester ([6,6]-PCBD), phenyl C71 butyric acid methyl ester (PC70BM), and phenyl C85 butyric acid methyl ester (PC84BM)), carbon nanotube (CNT), and poly (p-phenylenevinylene)-based polymers in which cyano groups are introduced (CN-PPV). The fullerene compounds are preferably used because of their high charge separation rates and electron transfer rates.

A hole-transporting layer may be provided between the positive electrode and the organic semiconductor layer in the photovoltaic device of this invention. Preferred materials for use in the hole-transporting layer are electrically conductive polymers such as polythiophene-based polymers, polyp-phenylenevinylene)-based polymers, and polyfluorene-based polymers and low-molecular-weight organic compounds exhibiting the characteristics of a p-type semiconductor such as phthalocyanine derivatives (H2Pc, CuPc, ZnPc, etc.) and porphyrin derivatives. In particular, polyethylenedioxythiophene (PEDOT), which is a polythiophene-based polymer, or PEDOT to which polystyrene sulfonate (PSS) is added is preferred. The thickness of the hole-transporting layer is preferably in the range of 5 to 600 nm, more preferably in the range of 30 to 200 nm.

Further, an electron-transporting layer may be provided between the organic semiconductor layer and the negative electrode in the photovoltaic device of this invention. The materials for forming the electron-transporting layer are not especially limited and organic materials exhibiting the characteristics of an n-type semiconductor such as the aforementioned electron-accepting organic materials (NTCDA, PTCDA, PTCDI-C8H, oxazole derivatives, triazole derivatives, phenanthroline derivatives, phosphine oxide derivatives, fullerene compounds, CNT, CN-PVV, etc.) are preferably used. The thickness of the electron-transporting layer is preferably in the range of 5 to 600 nm, more preferably in the range of 30 to 200 nm.

In the photovoltaic device of this invention, two organic semiconductor layers or more may be stacked through one intermediate electrode or more to form a tandem junction; for example, a stacked structure such as substrate/positive electrode/first organic semiconductor layer/intermediate electrode/second organic semiconductor layer/negative electrode. The stacking like this can improve the open circuit voltage. The aforementioned hole-transporting layer may be provided between the positive electrode and the first organic semiconductor layer and between the intermediate electrode and the second organic semiconductor layer. The aforementioned hole-transporting layer may be provided between the first organic semiconductor layer and the intermediate electrode and between the second organic semiconductor layer and the negative electrode.

In the case of a stacked structure such as this, it is preferable that at least one of the organic semiconductor layers contains the compound of this invention represented by general formula (1) and the other layer contains an electron-donating organic material that differs in band gap from the electron-donating organic material of this invention in order not to lower the short circuit current. Examples of electron-donating organic materials of this kind include the electron-donating organic materials described earlier; conjugated polymers such as polythiophene-based polymers, poly(p-phenylenevinylene)-based polymers, poly(p-phenylene)-based polymers, polyfluorene-based polymers, polypyrrole-based polymers, polyaniline-based polymers, polyacetylene-based polymers, and polythienylenevinylene-based polymers, phthalocyanine derivatives such as H2-phthalocyanine (H2Pc), copper phthalocyanine (CuPc), and zinc phthalocyanine (ZnPc), porphyrin derivatives, triarylamine derivatives such as N.N'-diphenyl-N,N'-di(3-methylphenyl)-4,4'-diphenyl-1, diamine (TPD) and N,N'-dinaphthyl-N,N'-diphenyl-4,4'-diphenyl-1, diamine (NPD), carbazole derivatives such as 4,4'-di(carbazol-9-yl)biphenyl (CBP), and low-molecular-weight organic compounds such as oligothiophene derivatives (terthiophene, quaterthiophene, sexithiophene, octithiophene, etc.).

The material to be used for the intermediate electrode preferably exhibits high electrical conductivity and examples thereof include the materials described earlier; metals such as gold, platinum, chromium, lithium, magnesium, calcium, tin, silver, and aluminum, transparent oxides and composite oxides of indium, tin, and the like such as indium tin oxide (ITO) and indium zinc oxide (IZO), alloys and laminates of the foregoing metals, polyethylenedioxythiophene (PEDOT), and PEDOT to which polystyrene sulfonate (PSS) is added. The intermediate electrode preferably has a light-transmitting property and even materials of poor optical transparency can secure sufficient optical transparency by decreasing the film thickness in many cases.

The organic semiconductor layer may be formed by any of the known methods such as spin coating, blade coating, slit die coating, screen printing, bar coating, in-mold coating, decalcomania, dip coating, inkjet coating, spray coating, and vacuum deposition and the methods for controlling the film thickness and orientation may be selected according to the characteristics of the target semiconductor layer.

The compound of this invention or the organic semiconductor material of this invention containing the compound of this invention exhibits high charge mobility, solvent solubility, oxidation stability, and good film-forming properties and an organic semiconductor device using the said compound or the said organic semiconductor material also displays excellent characteristics. Examples of organic semiconductor devices that can make the most of the characteristics of the organic semiconductor material of this invention include organic field effect transistors and organic thin film solar cells. Further, these organic semiconductor devices can be incorporated in displays such as organic EL panels and electronic paper, liquid crystal displays, information tags, and large area sensors such as artificial electronic skin sheets and sheet type scanners.

EXAMPLES

This invention is explained in more detail hereinafter with reference to the examples. However, this invention is not limited to the examples and can be reduced to practice in various modes unless such a practice exceeds the gist of this invention.

Example 1

Synthesis of Compound 1-21

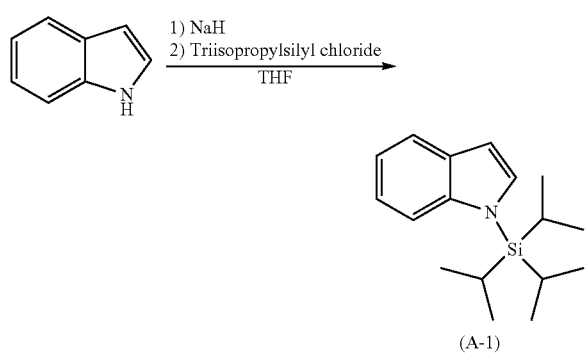

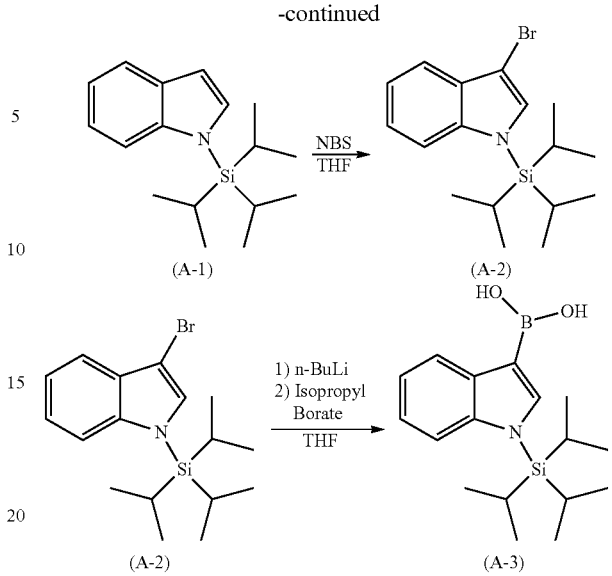

Under a nitrogen atmosphere, 60 ml of dehydrated tetrahydrofuran (THF) was added to 5.8 g (135 mmol) of sodium hydride (56.0% dispersion) and stirred at room temperature for 30 minutes. To the suspension thus obtained was added dropwise a solution of 13.4 g (114 mmol) of indole in THF (120 ml) over 30 minutes and, after completion of the dropwise addition, the mixture was stirred at room temperature for 30 minutes. To the resulting suspension was added 22.0 g (114 mol) of triisopropylsilyl chloride and the mixture was stirred at room temperature for 1.5 hours. The precipitated crystal was collected by filtration, the solvent was distilled off under reduced pressure, and Intermediate A-1 weighing 31.2 g (114 mmol, 100% yield) was obtained.

Under a nitrogen atmosphere, 100 ml of THF was added to 31.1 g (114 mmol) of Intermediate A, then a solution of 20.2 g (114 mmol) of N-bromosuccinimide in THF (70 ml) was added dropwise over 30 minutes, and after completion of the dropwise addition, the mixture was stirred at room temperature for 2 hours. The reaction solution was stripped of the solvent under reduced pressure, 90.0 g of dichloromethane was added to the residue, and the mixture was left standing for 1 hour. The precipitated crystal was collected by filtration and the solvent was distilled off under reduced pressure. To the residue thus obtained was added 100 ml of ethanol and the mixture was stirred at room temperature overnight. The precipitated solid was collected by filtration and Intermediate A-2 weighing 34.5 g (98 mmol, 86% yield) was obtained.

Under a nitrogen atmosphere, 200 ml of THF was added to 33.7 g (96 mmol) of Intermediate A-2 and cooled to −60° C., 72 ml of a hexane solution of n-butyllithium (1.57 mol/l) was added dropwise, and the mixture was stirred for 1 hour. Then, 21.7 g (115 mmol) of isopropyl borate was added and the mixture was stirred for 1 hour. The reaction solution was returned to room temperature and 100 ml of a saturated aqueous solution of ammonium chloride and 100 ml of toluene were added. The organic layer was washed with distilled water (3×200 ml) and dried over anhydrous magnesium sulfate, the magnesium sulfate was separated by filtration, the solvent was distilled off under reduced pressure, and Intermediate A-3 weighing 27.3 g (86 mmol, 90% yield) was obtained.

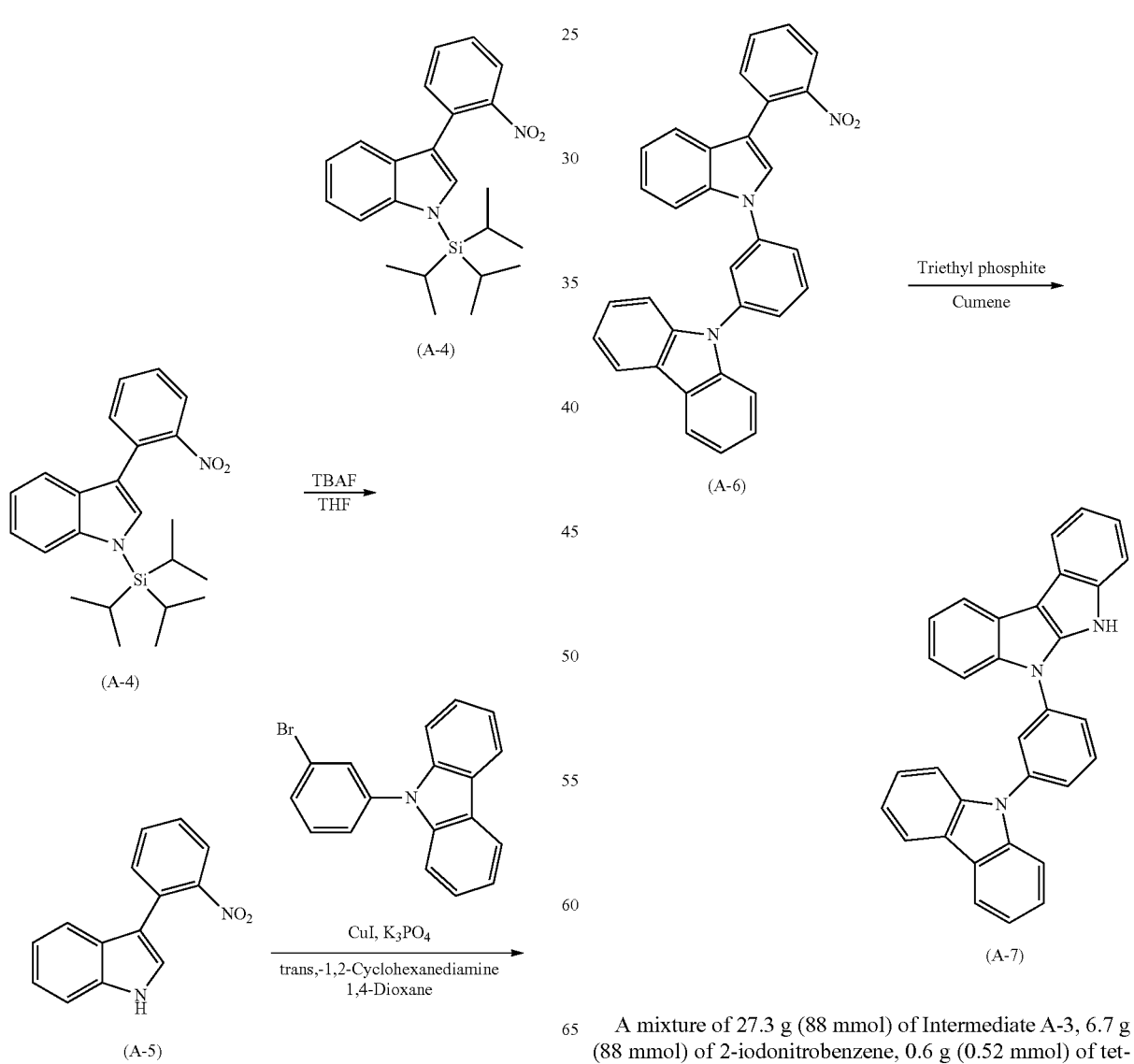
A mixture of 27.3 g (88 mmol) of Intermediate A-3, 6.7 g (88 mmol) of 2-iodonitrobenzene, 0.6 g (0.52 mmol) of tetrakis(triphenylphosphine)palladium(0), a solution of 17 g of sodium carbonate in water (80 ml), 200 ml of toluene, and 100 ml of ethanol was prepared and heated at 90° C. with stirring overnight. The reaction solution was cooled to room temperature and distilled water (100 ml) was added with stirring. The organic layer was washed with distilled water (3×100 ml) and dried over anhydrous magnesium sulfate, the magnesium sulfate was separated by filtration, and the solvent was distilled off under reduced pressure. To the residue was added 150 ml of methanol and the mixture was stirred at room temperature for 60 minutes. The precipitated solid was collected by filtration and Intermediate A-4 weighing 30.0 g (76 mmol, 87% yield) was obtained.

To 30.0 g (76 mmol) of Intermediate A-4 and 2.4 g (7.6 mmol) of tetrabutylammonium fluoride trihydrate (TBAF) was added 200 ml of THF and stirred at room temperature for 1 hour. Distilled water (100 ml) and toluene (100 ml) were added to the reaction solution and the mixture was stirred and separated into an aqueous layer and an organic layer. The organic layer was extracted with toluene (2×100 ml) and the extracts were combined and dried over anhydrous magnesium sulfate, the magnesium sulfate was separated by filtration, the solvent was distilled off under reduced pressure, and Intermediate A-5 was obtained. To Intermediate A-5 thus obtained were added 24.5 g (76 mmol) of 1-bromo-3-(N-carbazolyl)benzene, 2.4 g (13 mmol) of copper iodide, 79 g (372 mmol) of tripotassium phosphate, 14.2 g (124 mmol) of trans-1,2-cyclohexanediamine, and 500 ml of 1,4-dioxane and the mixture was heated at 120° C. with stirring for 10 hours. The reaction solution was cooled to room temperature, the precipitated crystal was collected by filtration, and the solvent was distilled off under reduced pressure. The residue was purified by silica gel column chromatography and Intermediate A-6 weighing 35.9 g (75 mol, 99% yield) was obtained.

A mixture of 35.9 g (75 mmol) of Intermediate A-6, 49.9 g (300 mmol) of triethyl phosphite, and 200 g of cumene was prepared and heated at 160° C. with stirring for 17 hours. The reaction solution was cooled to room temperature and the solvent was distilled off under reduced pressure. The residue was purified by silica gel column chromatography and Intermediate A-7 weighing 30.2 g (67.5 mmol, 90% yield) was obtained.

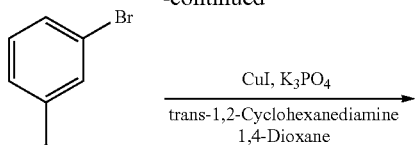

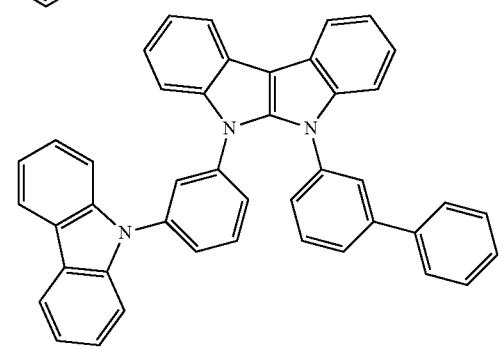

1-21

Under a nitrogen atmosphere, a mixture of 2.4 g (5.4 mmol) of Intermediate A-7, 1.4 g (5.9 mmol) of 3-bromobiphenyl, 0.2 g (1.1 mmol) of copper iodide, 3.1 g (26.8 mmol) of tripotassium phosphate, 1.1 g (5.3 mmol) of trans-1,2-cyclohexanediamine, and 30 ml of 1,4-dioxane was prepared and heated at 120° C. with stirring for 72 hours. The reaction solution was cooled to room temperature, the precipitated crystal was collected by filtration, and the solvent was distilled off under reduced pressure. The residue was purified by silica gel column chromatography and Compound 1-21 weighing 1.2 g (2.0 mmol, 37% yield) was obtained as a white solid.

Figure 6:
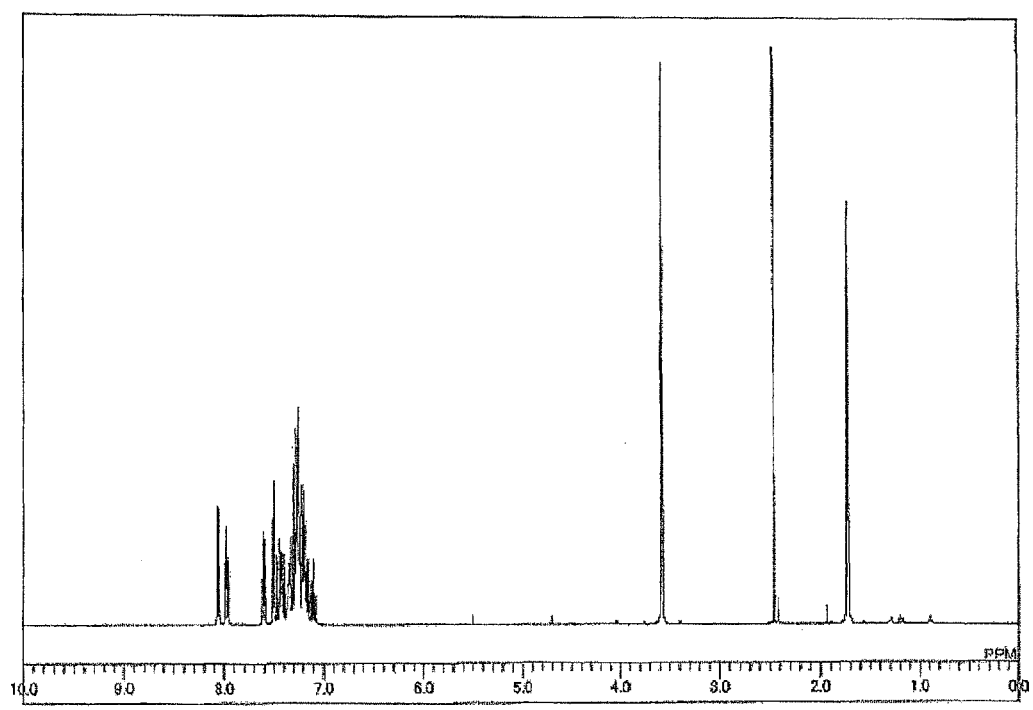
FIG. 6 is a $^1$H-NMR chart of Compound 1-21.

APCI-TOFMS: m/z 600 [M+H]$^+$. The result of $^1$H-NMR measurement (solvent: THF-d8) is shown in FIG. 6.

Example 2

Synthesis of Compound 1-29

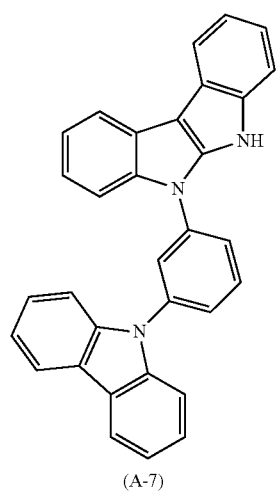

(A-7)

+

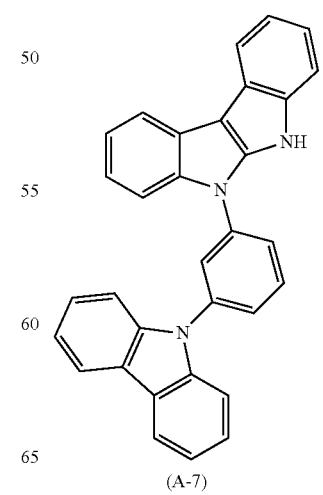

(A-7)

-continued

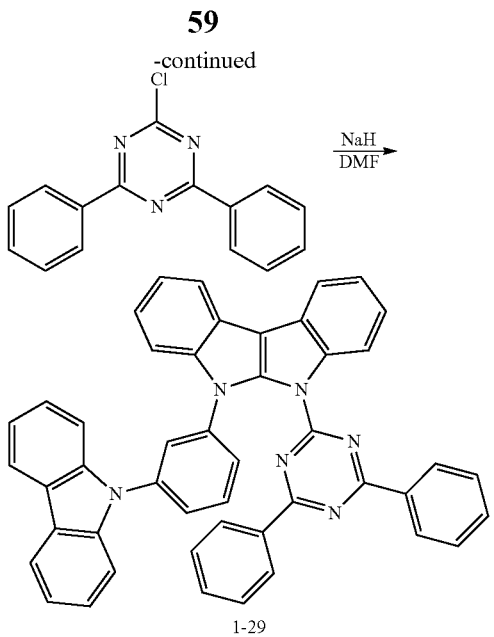

1-29

Under a nitrogen atmosphere, 10 ml of dehydrated N,N-dimethylformamide (DMF) was added to 0.2 g (5.9 mmol) of sodium hydride (62.2% dispersion) and stirred at room temperature for 30 minutes. To the suspension thus obtained was added a solution of 2.4 g (5.4 mmol) of Intermediate A-7 in DMF (10 ml) and the mixture was stirred at room temperature for 30 minutes. To the resulting suspension was added 1.4 g (5.4 mmol) of 2-chloro-4,6-diphenyl-1,3,5-triazine and the mixture was stirred at 60° C. for 30 minutes. The reaction solution was cooled to room temperature, distilled water (100 ml) was added with stirring, and the precipitated solid was collected by filtration. The solid was purified by silica gel column chromatography and hot reslurrying and Compound 1-29 weighing 1.8 g (2.6 mmol, 48% yield) was obtained as a yellow solid.

Figure 7:
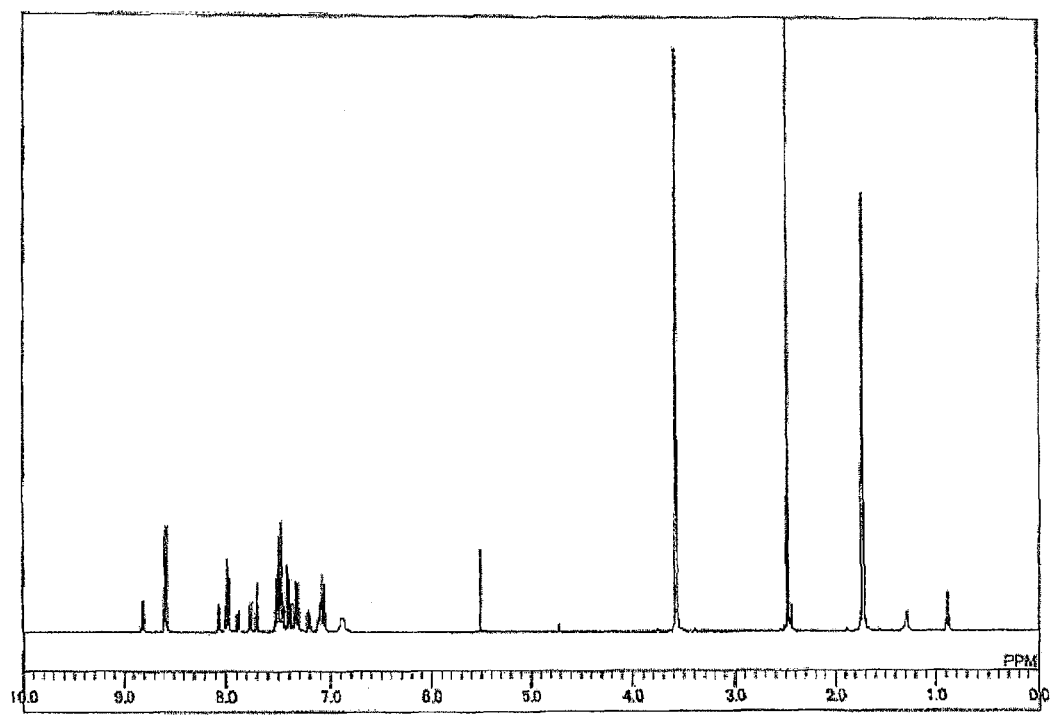
FIG. 7 is a $^1$H-NMR chart of Compound 1-29.

APCI-TOFMS: m/z 679 [M+H]$^+$. The result of $^1$H-NMR measurement (solvent: THF-d8) is shown in FIG. 7.

Example 3

Synthesis of Compound 1-30

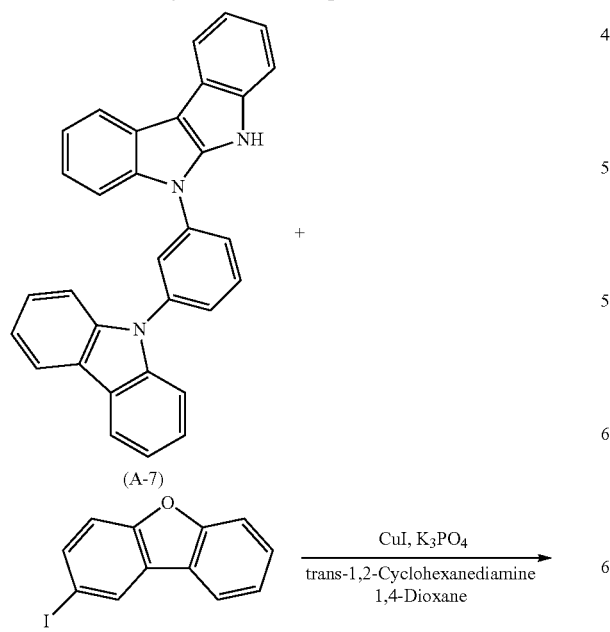

-continued

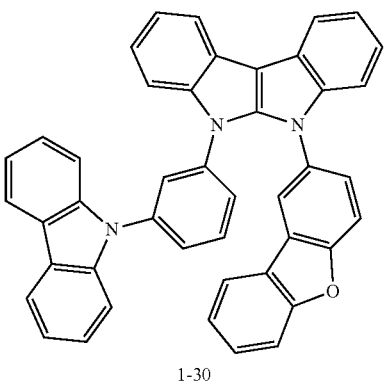

1-30

Compound 1-30 weighing 1.4 g (2.3 mmol, 43% yield) was obtained as a white solid as in the synthesis of Compound 1-21 except that 2-iododibenzofuran was used in place of 3-bromobiphenyl.

APCI-TOFMS: m/z 614 [M+H]$^+$.

Example 4

Synthesis of Compound 1-31

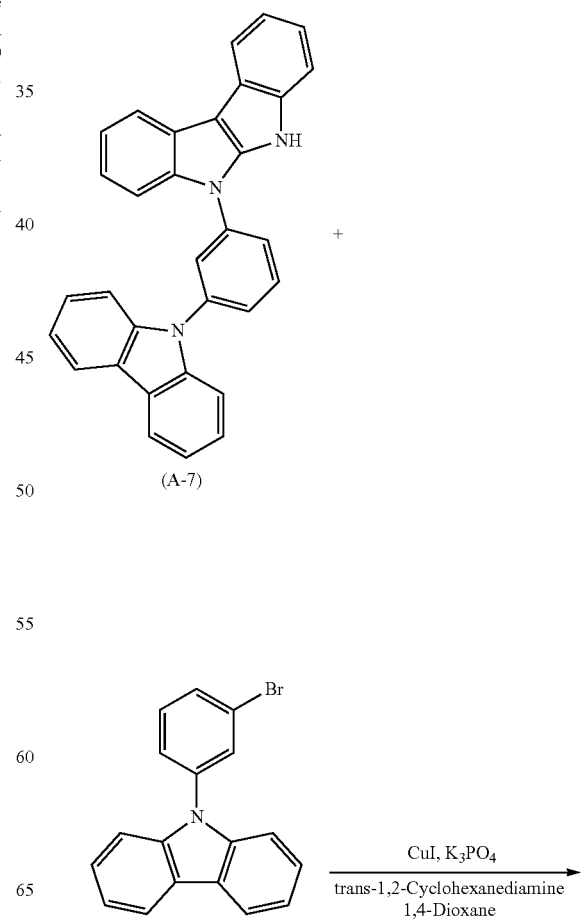

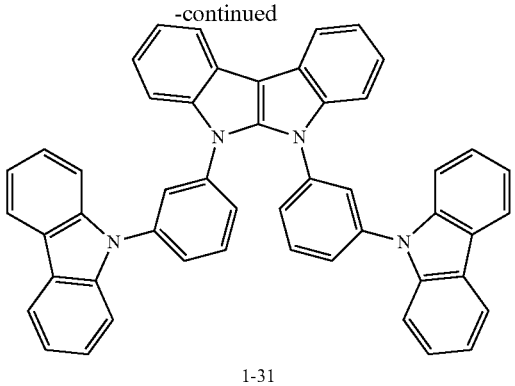

1-31

Compound 1-31 weighing 2.2 g (3.2 mmol, 59% yield) was obtained as a white solid as in the synthesis of Compound 1-21 except that 1-bromo-3-(N-carbazolyl)benzene was used in place of 3-bromobiphenyl.

APCI-TOFMS: m/z 689 [M+H]$^+$.

Example 5

Synthesis of Compound 1-52

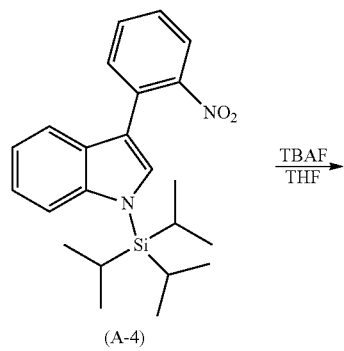

(A-4)

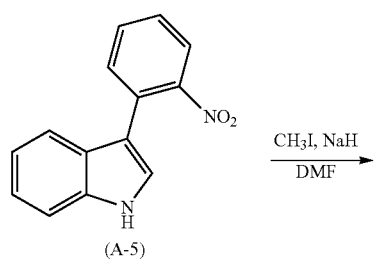

(A-5)

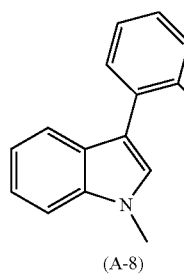

(A-8)

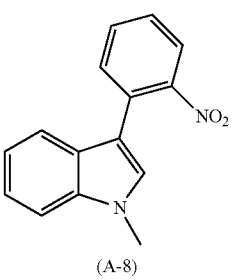

(A-8)

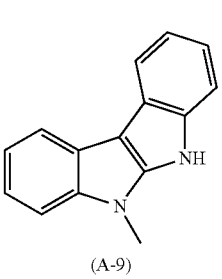

(A-9)

A mixture of 3.0 g (7.6 mmol) of Intermediate A-4, 0.2 g (0.76 mmol) of TBAF, and 20 ml of THF was prepared and stirred at room temperature for 1 hour. Distilled water (10 ml) and toluene (10 ml) were added to the reaction mixture and the mixture was stirred and separated into an aqueous layer and an organic layer. The organic layer was extracted with toluene (2×10 ml) and the extracts were combined and dried over anhydrous magnesium sulfate, the magnesium sulfate was separated by filtration, the solvent was distilled off under reduced pressure, and Intermediate A-5 was obtained. Then, under a nitrogen atmosphere, 0.2 g (9.1 mmol) of sodium hydride (56.0% dispersion) and 17 ml of DMF were stirred at room temperature for 30 minutes. To the suspension thus obtained was added dropwise a solution of 1.8 g (7.6 mmol) of Intermediate A-5 in DMF (17 ml) over 30 minutes and then the mixture was stirred at room temperature for 30 minutes. To the resulting suspension was added 1.3 g of iodomethane and the mixture was stirred at room temperature for 5 hours. Distilled water (20 ml) and hexane (20 ml) were added to the reaction solution, the organic layer was extracted, the extract was dried over anhydrous magnesium sulfate, and the magnesium sulfate was separated by filtration. The solvent was distilled off under reduced pressure and Intermediate A-8 weighing 1.5 g (114 mmol, 100% yield) was obtained.

Intermediate A-9 was obtained as in the synthesis of Intermediate A-7 except that Intermediate A-8 was used in place of Intermediate A-6.

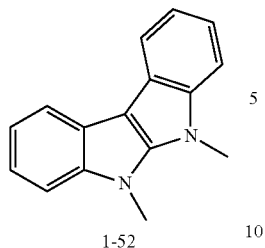

1-52

Under a nitrogen atmosphere, 1.2 ml of DMF was added to 0.02 g (0.5 mmol) of sodium hydride (60.5% dispersion) and stirred at room temperature for 30 minutes. To the suspension thus obtained was added a solution of 0.1 g (0.5 mmol) of Intermediate A-9 in DMF (1.0 ml) and the mixture was stirred at room temperature or 30 minutes. To the resulting suspension were added 0.08 g (0.5 mmol) of iodomethane and the mixture was stirred at room temperature for 2 hours. Distilled water (10 ml) was added to the reaction solution with stirring and the precipitated solid was collected by filtration. The solid was purified by reslurrying and Compound 1-52 weighing 0.09 g (0.4 mmol, 82% yield) was obtained as a white solid.

APCI-TOFMS: m/z 234 [M+H]$^+$.

Example 6

Synthesis of Compound 1-46

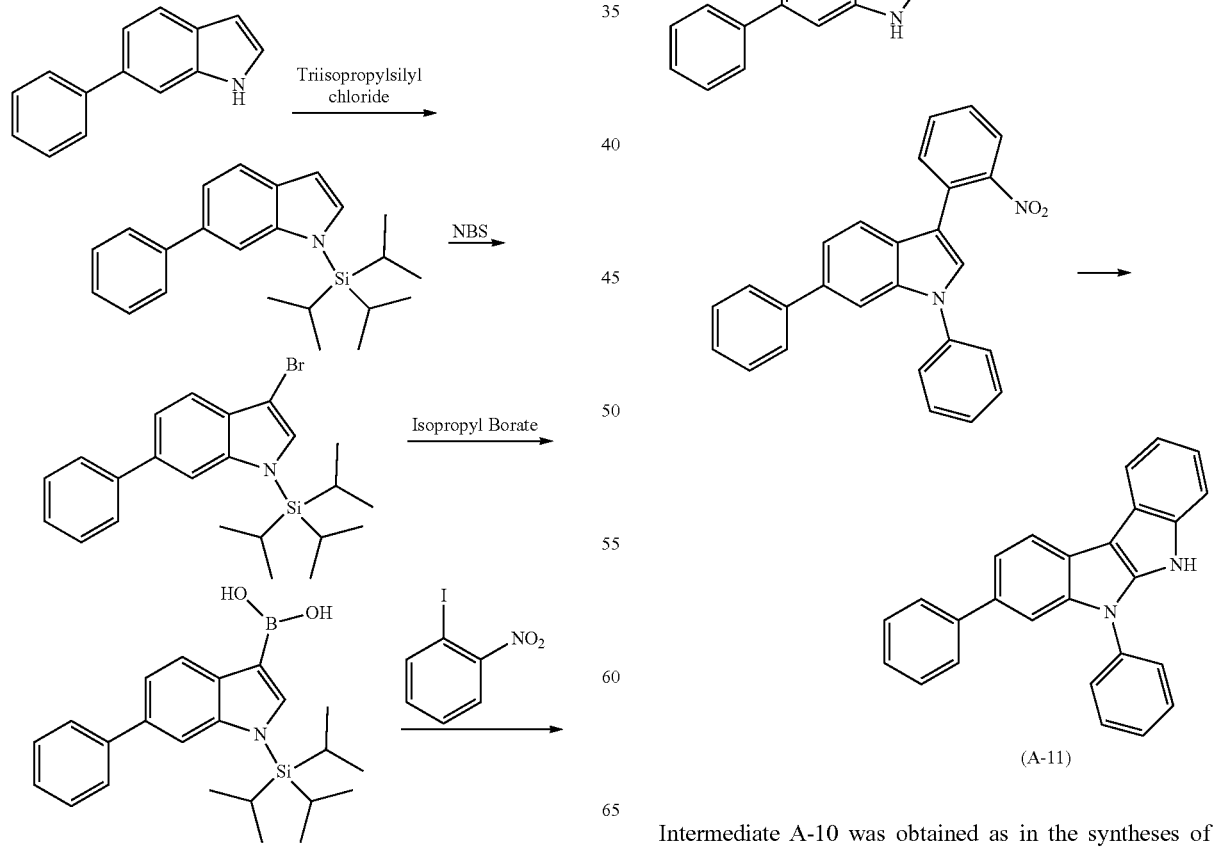

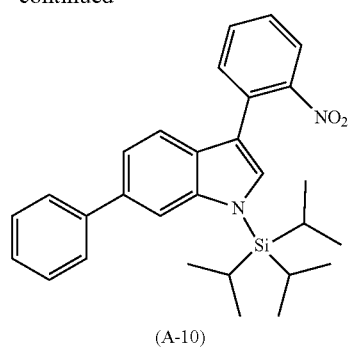

Intermediate A-10 was obtained as in the syntheses of Intermediates A-2, A-3, and A-4 except that 6-phenylindole was used in place of indole and iodobenzene was used in place of 1-bromo-3-(N-carbazolyl)benzene.

Intermediate A-11 was obtained as in the syntheses of Intermediates A-5, A-6, and A-7 except that Intermediate A-10 was used in place of Intermediate A-4 and iodobenzene was used in place of 1-bromo-3-(N-carbazolyl)benzene.

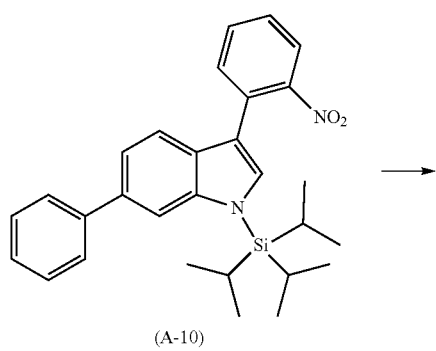

Compound 1-46 weighing 0.2 g (0.4 mmol, 73% yield) was obtained as a white solid as in the synthesis of Compound 1-52 except that Intermediate A-11 was used in place of Intermediate A-7 and 1-iodooctane was used in place of iodomethane.

APCI-TOFMS: m/z 471 [M+H]$^+$.

Example 7

Synthesis of Compound 1-45

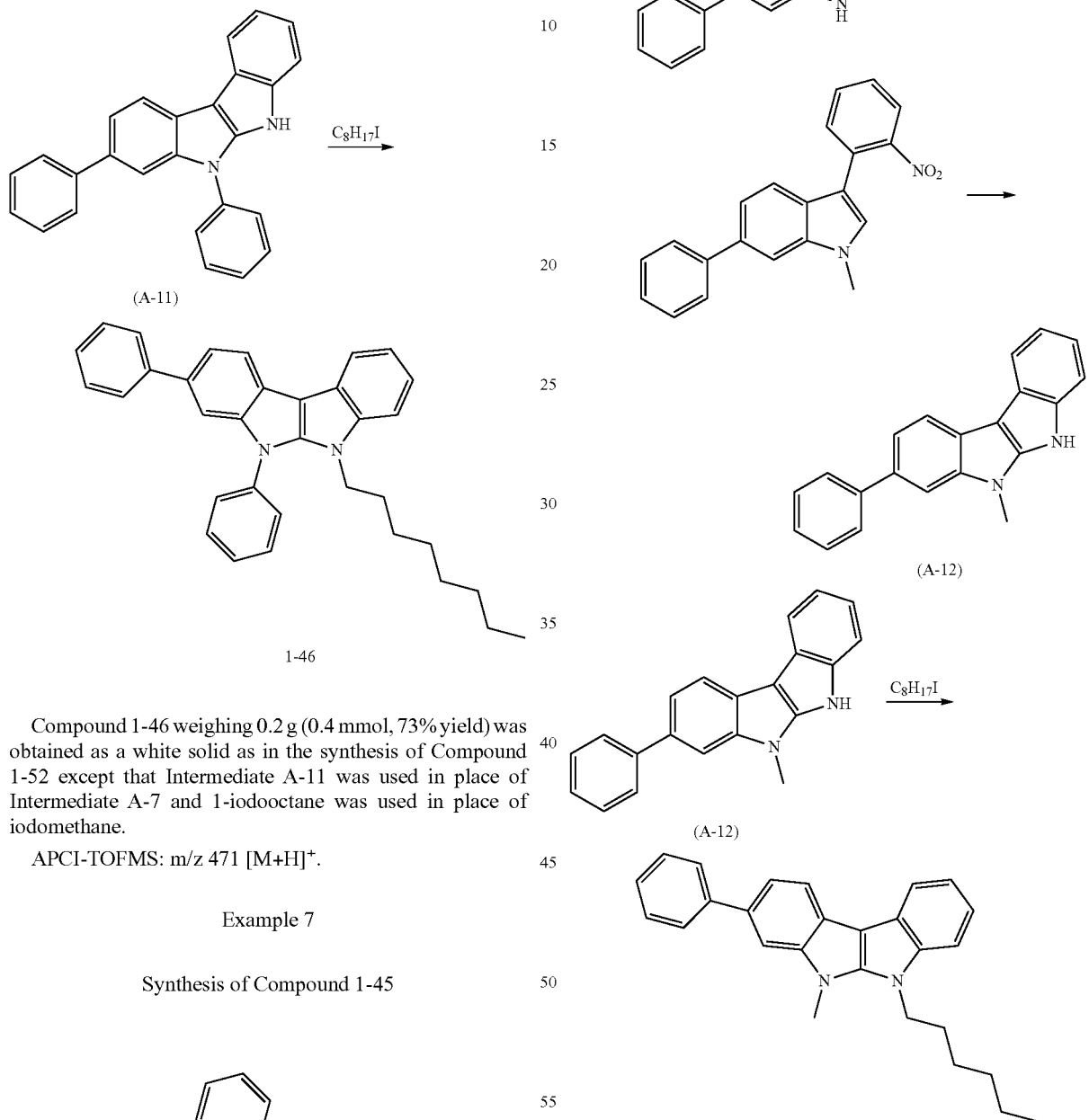

Intermediate A-12 was obtained as in the syntheses of Intermediates A-5, A-6, and A-7 except that Intermediate A-10 was used in place of Intermediate A-4 and iodomethane was used in place of 1-bromo-3-(N-carbazolyl)benzene.

Compound 1-45 weighing 0.16 g (0.4 mmol, 80% yield) was obtained as a white solid as in the synthesis of Compound 1-52 except that Intermediate A-12 was used in place of Intermediate A-7 and 1-iodooctane was used in place of iodomethane.
APCI-TOFMS: m/z 409 [M+H]$^+$.
Example 8
Synthesis of Compound 1-58
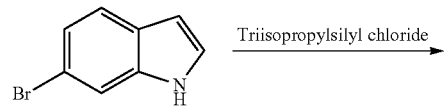
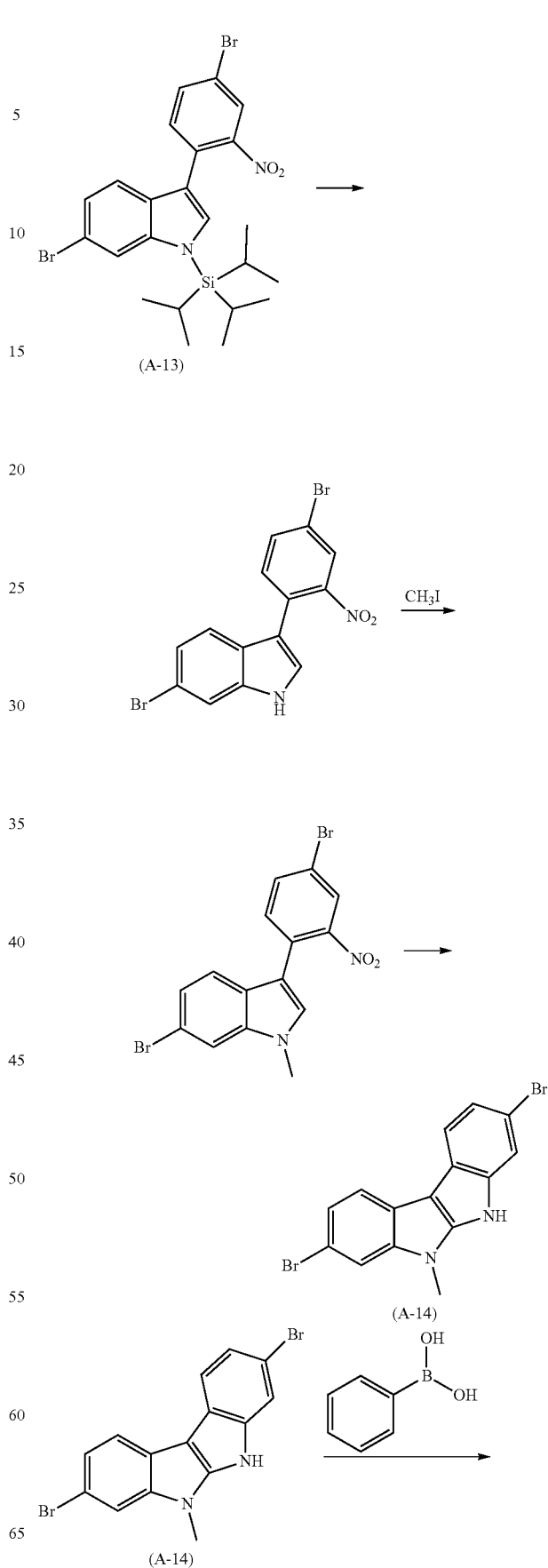
Intermediate A-13 was obtained as in the syntheses of Intermediates A-1, A-2, A-3, and A-4 except that 6-bromoindole was used in place of indole and 2-iodo-4-bromonitrobenzene was used in place of 2-iodonitrobenzene.

-continued

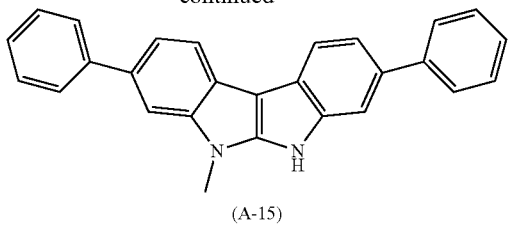

(A-15)

Intermediate A-14 was obtained as in the syntheses of Intermediates A-5, A-8, and A-9 except that Intermediate A-13 was used in place of Intermediate A-4.

Under a nitrogen atmosphere, a mixture of 6.2 g (16 mmol) of Intermediate A-14, 10.0 g (82 mmol) of phenylboronic acid, 1.0 g (8.2 mol) of tetrakis(triphenylphosphine)palladium(0), 200 ml of toluene, and 100 ml of ethanol was prepared and stirred. To the resulting mixture was added a solution of 30.5 g (0.33 mol) of sodium carbonate in 200 ml of water and the mixture was stirred at 100° C. for 5 hours. The reaction solution was cooled to room temperature. The organic layer was washed with distilled water (2×100 ml) and then dried over anhydrous magnesium sulfate, the magnesium sulfate was separated by filtration, and the solvent was distilled off under reduced pressure. The residue was purified by column chromatography and Intermediate A-15 weighing 3.9 g (10 mmol, 63% yield) was obtained.

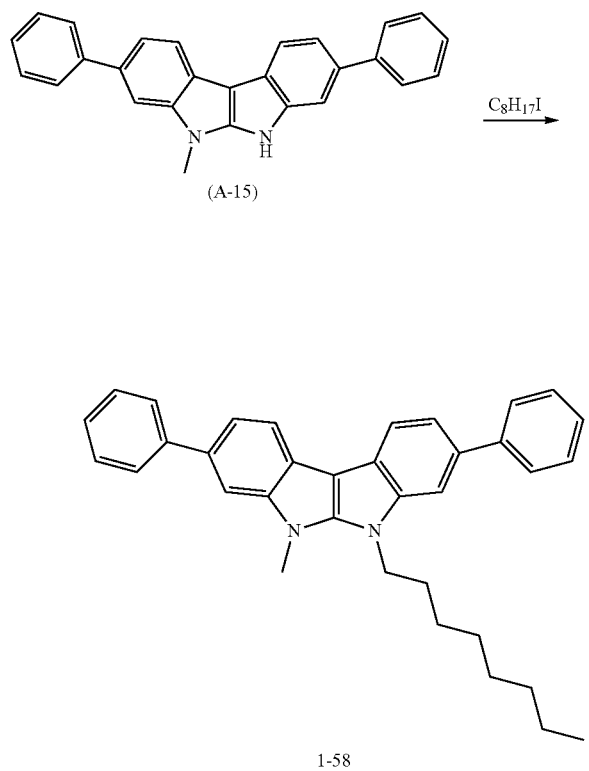

1-58

Compound 1-58 weighing 1.8 g (3.7 mmol, 65% yield) was obtained as a white solid as in the synthesis of Compound 1-52 except that Intermediate A-15 was used in place of Intermediate A-9 and 1-iodooctane was used in place of iodomethane.

APCI-TOFMS: m/z 485 $[M+H]^+$.

Example 9

Synthesis of Compound 3-3

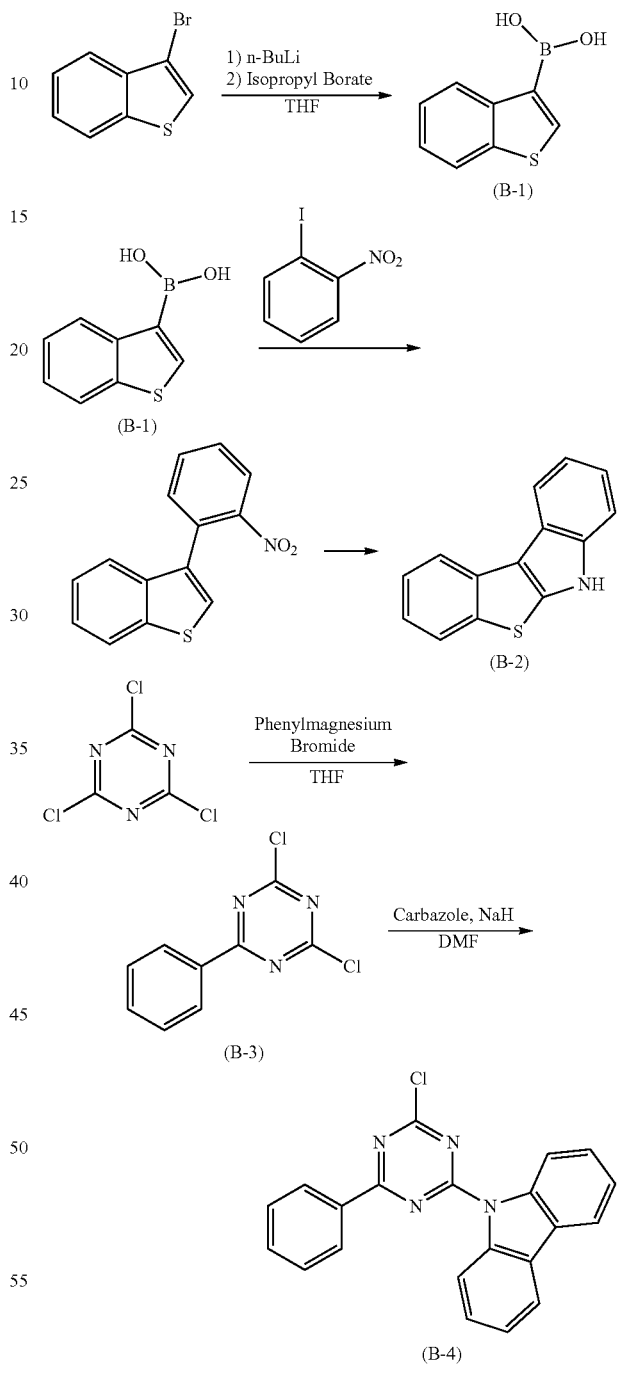

Under a nitrogen atmosphere, 100 ml of THF was added to 10 g (47 mmol) of 3-bromobenzothiophene and cooled to −60° C., 36 ml of a hexane solution of n-butyllithium (1.57 mol/l) was added dropwise, and the mixture was stirred for 1 hour. Then, 13.3 g (71 mmol) of triiospropyl borate was added and the stirring was continued for 1 hour. The reaction solution was returned to room temperature and 50 ml of a saturated aqueous solution of ammonium chloride and 100 ml of toluene were added. The organic layer was washed with distilled water (3×100 ml) and dried over anhydrous magnesium sulfate, the magnesium sulfate was separated by filtration, the solvent was distilled off under reduced pressure, and Intermediate B-1 weighing 6.9 g (39 mmol, 83% yield) was obtained.

Intermediate B-2 was obtained as in the syntheses of Intermediates A-4 and A-7 except that Intermediate B-1 was used in place of Intermediate A-3.

To 10 g (54 mmol) of cyanuric chloride was added 50 ml of THF, then 54 ml of a THF solution of phenylmagnesium bromide (1.0 mol/l) was added dropwise, and the mixture was stirred at 0° C. for 3 hours. To the reaction solution were added 50 ml of distilled water and 100 ml of toluene, the mixture was separated into an aqueous layer and an organic layer, the organic layer was dried over anhydrous magnesium sulfate, the magnesium sulfate was separated by filtration, and the solvent was distilled off under reduced pressure. The solid thus obtained was washed with hexane and Intermediate B-3 was obtained. Then, under a nitrogen atmosphere, 30 ml of THF was added to 1.3 g (34 mmol) of sodium hydride (62.2% dispersion) and stirred at room temperature for 30 minutes. To the suspension thus obtained was added a solution of 5.5 g (32 mmol) of carbazole in DMF (20 ml) and the mixture was stirred at room temperature for 30 minutes. To the resulting suspension was added 7.0 g (31 mmol) of Intermediate B-3 and stirred at 60° C. for 30 minutes. The reaction solution was cooled to room temperature, distilled water (100 ml) was added with stirring, and the precipitated solid was collected by filtration. The solid was purified by silica gel column chromatography and hot reslurrying and Intermediate B-4 weighing 8.1 g (23 mmol, 74% yield) was obtained.

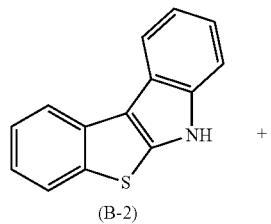

(B-2)

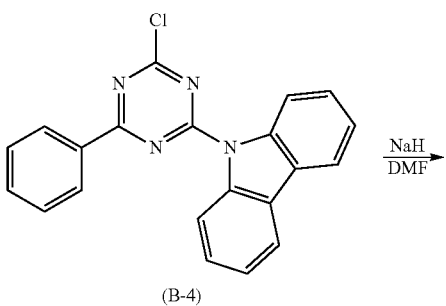

(B-4)

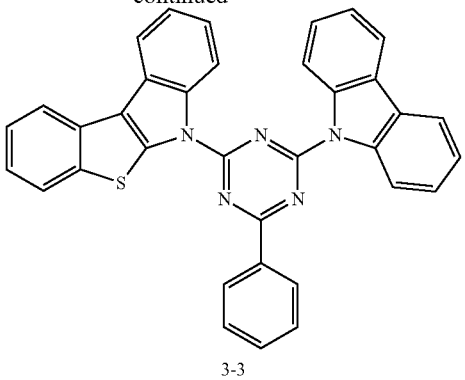

3-3

Compound 3-3 weighing 3.8 g (6.9 mmol, 62% yield) was obtained as a white solid as in the synthesis of Compound 1-29 except that Intermediate W was used in place of Intermediate A-7 and Intermediate B-4 was used in place of 2-chloro-4,6-diphenyl-1,3,5-triazine.

APCI-TOFMS: m/z 544 [M+H]$^+$.

Example 10

Synthesis of Compound 2-3

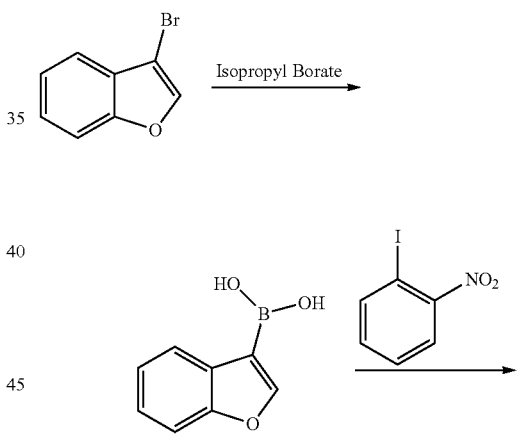

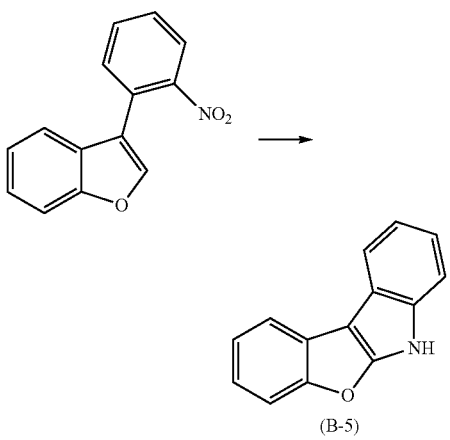

(B-5)

-continued

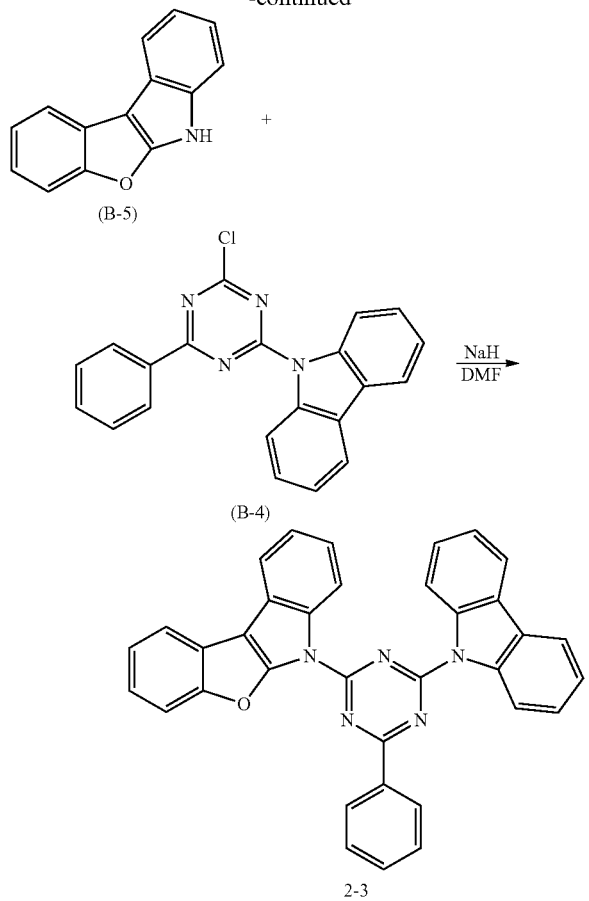

Intermediate B-5 was obtained as in the syntheses of Intermediates B-1 and B-2 except that 3-bromobenzofuran was used in place of 3-bromobenzothiophene.

Compound 2-3 weighing 3.9 g (7.4 mmol, 74% yield) was obtained as a white solid as in the synthesis of Compound 3-3 except that Intermediate B-5 was used in place of Intermediate B-2.

APCI-TOFMS: m/z 528 [M+H]$^+$.

Example 11

The constituent layers were deposited in thin film by the vacuum deposition process at a degree of vacuum of $4.0 \times 10^{-5}$ Pa one upon another on a glass substrate on which a 110 nm-thick ITO anode had been formed. First, copper phthalocyanine (CuPc) was deposited on the ITO anode to a thickness of 25 nm. Then, 4,4'-bis[N-(1-naphthyl)-N-phenylamino]biphenyl (NPB) was deposited to a thickness of 40 nm as a hole-transporting layer. Next, Compound 1-21 obtained in Synthetic Example 1 as a host material and tris(2-phenylpyridine)iridium(III) (Ir(ppy)$_3$) as a phosphorescent dopant were co-deposited from different deposition sources to a thickness of 40 nm to form a light-emitting layer. The concentration of Ir(ppy)$_3$ in the light-emitting layer was 10.0 wt %. Next, tris(8-hydroxyquinolinato)aluminum (III) (Alq3) was deposited to a thickness of 20 nm as an electron-transporting layer. Further, lithium fluoride (LiF) was deposited on the electron-transporting layer to a thickness of 1.0 nm as an electron-injecting layer. Finally, aluminum (Al) was deposited as an electrode on the electron-injecting layer to a thickness of 70 nm to finish the fabrication of an organic EL device.

The organic EL device thus fabricated was connected to an external power source and, when direct current voltage was applied, the device was confirmed to have the luminous characteristics shown in Table 1. In Table 1, the values of the luminance, voltage, and luminous efficiency are those obtained when the device was driven at 10 mA/cm$^2$. The peak wavelength of the spectrum of light emitted from the device is 530 nm and this proves that light is emitted from Ir(ppy)$_3$.

Example 12

An organic EL device was fabricated as in Example 11 except that Compound 1-30 was used as the host material in the light-emitting layer.

Example 13

An organic EL device was fabricated as in Example 11 except that Compound 1-31 was used as the host material in the light-emitting layer.

Comparative Example 1

An organic EL device was fabricated as in Example 11 except that 4,4'-bis(9-carbazolyl)biphenyl (CBP) was used as the host material in the light-emitting layer.

The peak wavelength of the spectrum of light emitted from each of the devices fabricated in Examples 11 to 13 and Comparative Example 1 is 530 nm and this proves that light is emitted from Ir(ppy)$_3$. The luminous characteristics are shown in Table 1.

TABLE 1

| | | luminous characteristics (@10 mA/cm$^2$) | | |
|---|---|---|---|---|
| | host material | luminance (cd/m$^2$) | voltage (V) | luminous efficiency (lm/W) |
| Example 11 | 1-21 | 2950 | 8.5 | 10.9 |
| Example 12 | 1-30 | 3100 | 9.0 | 10.8 |
| Example 13 | 1-31 | 2730 | 8.8 | 9.7 |
| Comparative Example 1 | CBP | 2420 | 9.3 | 8.2 |

Example 14

The constituent layers were deposited in thin film by the vacuum deposition process at a degree of vacuum of $4.0 \times 10^{-5}$ Pa one upon another on a glass substrate on which a 110 nm-thick ITO anode had been formed. First, copper phthalocyanine (CuPc) was deposited on the ITO anode to a thickness of 25 nm. Then, 4,4'-bis[N-(1-naphthyl)-N-phenylamino]biphenyl (NPB) was deposited to a thickness of 55 nm as a hole-transporting layer. Next, Compound 1-29 obtained in Synthetic Example 2 as a host material and bis(2-(2'-benzo[4,5-a]thienyl)pyridinato-N, C3)iridium (acetylacetonate) [(Btp)$_2$Iracac] as a phosphorescent dopant were co-deposited from different deposition sources to a thickness of 47.5 nm to form a light-emitting layer. The concentration of (Btp)$_2$Iracac in the light-emitting layer was 8.0 wt %. Next, tris(8-hydroxyquinolinato)aluminum (III) (Alq3) was deposited to a thickness of 30 nm as an electron-transporting layer. Further, lithium fluoride (LiF) was deposited on the electron-transporting layer to a thickness of 1.0 nm as an electron-injecting layer. Finally, aluminum (Al) was deposited as an electrode on the electron-injecting layer to a thickness of 200 nm to finish the fabrication of an organic EL device.

The organic EL device thus fabricated was connected to an external power source and, when direct current voltage was applied, the device was confirmed to have the luminous characteristics shown in Table 2. In Table 2, the values of the luminance, voltage, and luminous efficiency are those obtained when the device was driven at 10 mA/cm$^2$.

Example 15

An organic EL device was fabricated as in Example 14 except that Compound 1-30 was used as the host material in the light-emitting layer.

Example 16

An organic EL device was fabricated as in Example 14 except that Compound 3-3 was used as the host material in the light-emitting layer.

Comparative Example 2

An organic EL device was fabricated as in Example 14 except that bis(2-methyl-8-quinolinolato)-4-phenylphenolatoaluminum(III) (BAlq) was used as the host material in the light-emitting layer.

The peak wavelength of the spectrum of light emitted from each of the devices fabricated in Examples 14 to 16 and Comparative Example 2 is 620 nm and this proves that light is emitted from (Btp)$_2$Iracac. The luminous characteristics are shown in Table 2.

TABLE 2

| | | luminous characteristics (@10 mA/cm$^2$) | | |
|---|---|---|---|---|
| | host material | luminance (cd/m$^2$) | voltage (V) | luminous efficiency (lm/W) |
| example14 | 1-29 | 1100 | 7.8 | 3.9 |
| example15 | 1-30 | 1240 | 5.9 | 5.9 |
| example16 | 3-3 | 1279 | 5.9 | 6.1 |
| Comparative Example 2 | BAlq | 1020 | 8.4 | 3.8 |

It is apparent from Tables 1 and 2 that the nitrogen-containing aromatic compounds of this invention, when used in organic EL devices, show good luminous characteristics in comparison with CBP or BAlq, a compound generally known as a phosphorescent host.

Example 17

The characteristics of the organic semiconductor material of this invention were evaluated by fabricating an organic TFT device having the structure illustrated in FIG. 2. First, a silicon wafer (n-doped) that has a layer of thermally grown silicon oxide with a thickness of approximately 300 nm was cleaned with a mixture of sulfuric acid and aqueous hydrogen peroxide, boiled in isopropyl alcohol, and dried. The silicon wafer thus obtained was spin-coated with a photoresist, exposed to light through a photomask in an exposure machine, developed in a developer, washed with deionized water, and dried in air. On this patterned silicon wafer was deposited chromium to a thickness of 3 nm and gold was further deposited on the chromium to a thickness of 50 nm by the vacuum deposition technique. The silicon wafer thus treated was immersed in a remover solution to build thereon a source electrode and a drain electrode. The silicon wafer on which the source electrode and the drain electrode are built was washed with acetone, further boiled in isopropyl alcohol, dried, and then immersed in an approximately 1×10$^{-6}$ M solution of octyltrichlorosilane in toluene overnight. Then, the silicon wafer was washed with toluene, then with isopropyl alcohol, and heated at 110° C. for approximately 10 minutes to furnish an octyltrichlorosilane (OTS)-treated organic TFT substrate having a channel length (L) of 25 μm and a channel width of 15.6 μm. Then, a 1 wt % solution of Compound 1-21 in chlorobenzene was filtered through a 0.2-μm syringe filter and applied to the OTS-treated substrate by spin coating at room temperature at a rotational speed of 1,000 rpm for 30 seconds. The substrate was then dried at 80° C. for 30 minutes. At this time, the thickness of the organic semiconductor layer was 50 nm. An organic TFT device having the structure shown in FIG. 2 was fabricated in this manner.

The transistor characteristics of the organic TFT device thus fabricated were evaluated by applying a voltage in the range of −10 to −100 V between the source electrode and the drain electrode, varying the gate voltage in the range of −30 to −80 V, and plotting the voltage-current curve at a temperature of 25° C. The electron field-effect mobility (μ) was calculated using the following equation (I) expressing the drain current $I_d$.

$$I_d = (W/2L)\mu C_i (V_g - V_t)^2 \quad (I)$$

In the aforementioned equation (I), L is the gate length, W is the gate width, $C_i$ is the capacity per unit area of the insulation layer, $V_g$ is the gate voltage, and $V_t$ is the threshold voltage. The on/off ratio was calculated from the ratio of the maximum drain current to the minimum drain current. The characteristics of the organic TFT device are shown in Table 3.

An organic TFT device was fabricated as in Example 17 except that a 1 wt % solution of Compound 1-58 in chloroform was used in place of the 1 wt % solution of Compound 1-21 in chlorobenzene and the spin coating was performed at room temperature at a rotational speed of 1,000 rpm for 30 seconds. The characteristics of the organic TFT devices thus fabricated are shown in Table 3

TABLE 3

| | Compound | mobility (cm$^2$/Vs) | on/off ratio |
|---|---|---|---|
| Example17 | 1-21 | 3.2 × 10$^{-4}$ | 10$^3$ |
| Example18 | 1-58 | 4.8 × 10$^{-2}$ | 10$^5$ |

It is apparent from Table 3 that the nitrogen-containing aromatic compounds of this invention have excellent characteristics as organic semiconductors.

INDUSTRIAL APPLICABILITY

The substituents introduced to the heterocycle fused to indole and to the nitrogen atom of indole in the skeleton of the nitrogen-containing aromatic compound of this invention seem to enable the compound to exercise control of a variety of energies such as ionization potential, electron affinity, and triplet excitation energy. The fused indole skeleton formed by a specified mode of fusion like this appears to provide high charge stability. Further, the nitrogen-containing aromatic compound of this invention is considered to have high charge transfer characteristics. Thus, it becomes possible for an organic electronic device using the nitrogen-containing aromatic compound of this invention to display excellent characteristics. The compound has a potentiality of finding use in displays such as organic EL panels and electronic paper, liquid crystal displays, organic field effect transistors, organic thin film solar cells, information tags, and large-area sensors such as artificial electronic skin sheets and sheet type scanners and has a high technical value.

The invention claimed is:

1. An organic electronic device characterized by using an organic semiconductor material containing a nitrogen-containing aromatic compound represented by general formula (1):

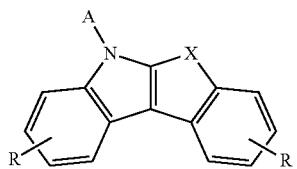

(1)

In general formula (1), X is N-A', O, S, or Se; A is an alkyl group of 1 to 30 carbon atoms, a cycloalkyl group of 3 to 30 carbon atoms, an alkenyl group of 2 to 30 carbon atoms, an alkynyl group of 2 to 30 carbon atoms, an aromatic hydrocarbon group of 6 to 30 carbon atoms, or an aromatic heterocyclic group of 3 to 30 carbon atoms exclusive of a heterocycle consisting of 4 rings or more; each R is independently a hydrogen atom, an alkyl group of 1 to 30 carbon atoms, a cycloalkyl group of 3 to 30 carbon atoms, an alkenyl group of 2 to 30 carbon atoms, an alkynyl group of 2 to 30 carbon atoms, an aromatic hydrocarbon group of 6 to 30 carbon atoms, or an aromatic heterocyclic group of 3 to 30 carbon atoms exclusive of a heterocycle consisting of 4 rings or more; and A' is an alkyl group of 1 to 30 carbon atoms, a cycloalkyl group of 3 to 30 carbon atoms, an alkenyl group of 2 to 30 carbon atoms, an alkynyl group of 2 to 30 carbon atoms, an aromatic heterocyclic group-substituted aromatic hydrocarbon group of 6 to 50 carbon atoms, or an aromatic heterocyclic group of 3 to 50 carbon atoms exclusive of a heterocycle consisting of 4 rings or more.

2. An organic electronic device as described in claim 1 wherein, in general formula (1), X is N-A'.

3. An organic electronic device as described in claim 1 wherein the organic electronic device is a light-emitting device, a thin film transistor, or a photovoltaic device.

4. An organic electronic device as described, in claim 3 wherein the light-emitting device is an organic electroluminescent device.

* * * * *